(12) United States Patent
Yang

(10) Patent No.: US 11,684,344 B2
(45) Date of Patent: Jun. 27, 2023

(54) SYSTEMS AND METHODS FOR QUANTITATIVE ABDOMINAL AORTIC ANEURYSM ANALYSIS USING 3D ULTRASOUND IMAGING

(71) Applicant: Verathon Inc., Bothell, WA (US)

(72) Inventor: Fuxing Yang, Bothell, WA (US)

(73) Assignee: VERATHON INC., Bothell, WA (US)

( * ) Notice: Subject to any disclaimer, the term of this patent is extended or adjusted under 35 U.S.C. 154(b) by 204 days.

(21) Appl. No.: 16/739,494

(22) Filed: Jan. 10, 2020

(65) Prior Publication Data

US 2020/0229796 A1  Jul. 23, 2020

Related U.S. Application Data

(60) Provisional application No. 62/793,501, filed on Jan. 17, 2019.

(51) Int. Cl.
*A61B 8/08* (2006.01)
*A61B 8/14* (2006.01)
(Continued)

(52) U.S. Cl.
CPC ............ *A61B 8/5223* (2013.01); *A61B 8/145* (2013.01); *A61B 8/466* (2013.01); *A61B 8/5246* (2013.01);
(Continued)

(58) Field of Classification Search
CPC ....... A61B 8/5223; A61B 8/145; A61B 8/466; A61B 8/5246; A61B 8/483; A61B 8/5207;
(Continued)

(56) References Cited

U.S. PATENT DOCUMENTS

| 8,012,090 B2 | 9/2011 | Steen |
| 8,133,181 B2 | 3/2012 | Yuk et al. |

(Continued)

FOREIGN PATENT DOCUMENTS

| CN | 105828723 A | 8/2016 |
| WO | 2018112063 A1 | 6/2018 |

OTHER PUBLICATIONS

Cootes et al., A Trainable Method of Parametric Shape Description, Image and Vision Computing, vol. 10, Issue 5, Jun. 1992, pp. 289-294, Received Oct. 10, 1991, Revised Jan. 16, 1992, Available online Jun. 10, 2003.*

(Continued)

*Primary Examiner* — Bo Joseph Peng
(74) *Attorney, Agent, or Firm* — Snyder, Clark, Lesch & Chung, LLP

(57) ABSTRACT

A system includes a probe configured to transmit ultrasound signals directed to a target blood vessel and receive echo information associated with the transmitted ultrasound signals. The system also includes at least one processing device configured to process the received echo information and generating a three-dimensional ultrasound image of the target blood vessel; obtain a three-dimensional vascular model corresponding to the target blood vessel; identify a best-fit of the three-dimensional vascular model onto the three-dimensional target image; store the best fit of the three-dimensional vascular model as a segmentation result; and calculate, based on the segmentation result, measurements for the target blood vessel.

20 Claims, 17 Drawing Sheets

(51) Int. Cl.
*A61B 8/00* (2006.01)
*G06N 3/084* (2023.01)
*G06T 7/00* (2017.01)

(52) U.S. Cl.
CPC ........... *G06N 3/084* (2013.01); *G06T 7/0012* (2013.01); *G06T 2207/10136* (2013.01); *G06T 2207/30101* (2013.01)

(58) Field of Classification Search
CPC .... A61B 8/5215; A61B 8/0891; G06N 3/084; G06T 7/0012; G06T 2207/10136; G06T 2207/30101; G06T 7/149
See application file for complete search history.

(56) References Cited

U.S. PATENT DOCUMENTS

| | | |
|---|---|---|
| 2004/0054280 A1 | 3/2004 | McMorrow et al. |
| 2005/0288584 A1 | 12/2005 | McMorrow et al. |
| 2006/0147114 A1* | 7/2006 | Kaus .................. G06T 7/12 382/173 |
| 2007/0103464 A1* | 5/2007 | Kaufman .................. G06T 7/64 345/424 |
| 2007/0276254 A1 | 11/2007 | Yang et al. |
| 2008/0249414 A1* | 10/2008 | Yang .................. A61B 8/0883 600/445 |
| 2009/0062644 A1 | 3/2009 | McMorrow et al. |
| 2010/0240996 A1* | 9/2010 | Ionasec .................. G06T 7/262 600/443 |
| 2013/0231564 A1* | 9/2013 | Zagorchev .............. G06T 7/62 600/447 |

OTHER PUBLICATIONS

Fenster, Aaron et al., "Three-dimensional ultrasound scanning," Interface Focus, Jun. 1, 2011, 17 pages.

Cusumano, Andrea et al., "Three-dimensional ultrasound imaging: Clinical applications," ScienceDirect, Ophthalmology, vol. 105, Issue 2, Feb. 1998, retrieved on Oct. 12, 2018, <https://www.sciencedirect.com/science/article/pii/S0161642098932110>.

Rouet, Laurence et al. "Semi-automatic abdominal aortic aneurysms geometry assessment based on 3D ultrasound," Ultrasonics Symposium (IUS), 2010 IEEE, Oct. 11, 2010, 3 pages.

Lesage, David et al. "A review of 3D vessel lumen segmentation techniques: Models, features and extraction schemes," Medical Image Analysis, Oxford University Press, Oxford, GB, vol. 13 No. 6, Dec. 1, 2009, 28 pages.

Moreau-Gaudry, Alexandre et al. "Active Model Based Carotid Ultrasonic Data Segmentation," Electronic Publishing, Artistic Imaging, and Digital Typography, Springer Verlag, DE, vol. 1679, Sep. 19, 1999, 8 pages.

International Search Report and Written Opinion issued in corresponding International Application No. PCT/US2020/013046, dated Apr. 28, 2020, 13 pages.

* cited by examiner

SYSTEMS AND METHODS FOR QUANTITATIVE ABDOMINAL AORTIC ANEURYSM ANALYSIS USING 3D ULTRASOUND IMAGING

CROSS-REFERENCE TO RELATED APPLICATION

This application claims priority under 35 U.S.C. § 119, based on U.S. Provisional Patent Application No. 62/793,501 filed Jan. 17, 2019, the disclosure of which is hereby incorporated by reference.

BACKGROUND INFORMATION

Abdominal aortic aneurysm (AAA) refers to a dilatation of the aorta between the diaphragm and the aortic bifurcation and, by convention, can be defined as an abdominal aortic diameter of thirty (30) millimeters or more in either anterior-posterior or transverse planes. Ultrasound imaging is a common modality for screening patients suffering from AAA. Although ultrasound imaging provides inexpensive and non-invasive real-time imaging, the image quality is lower compared with other imaging modalities, such as computed tomography (CT).

The most common clinical measure of AAA severity, which plays a major role in making a decision on surgical intervention, is the diameter of the aneurysm.

DETAILED DESCRIPTION OF PREFERRED EMBODIMENTS

The following detailed description refers to the accompanying drawings. The same reference numbers in different drawings may identify the same or similar elements. Also, the following detailed description does not limit the invention.

Current ultrasound examination of abdominal aortic aneurysms (AAA) uses anterior-posterior measurement derived from a single two-dimensional (2D) still image. A major source of error associated with this method is that investigators will orientate the image plane differently. Furthermore, agreement between ultrasound and computed tomography (CT) is known to be inadequate.

Implementations described herein relate to using ultrasound imaging for identifying an abdominal aorta, which may include an aneurysm. In accordance with one exemplary implementation, ultrasound imaging of the abdominal aorta may be performed without the need for manual segmentation of the aorta and without using other imaging modalities, such as CT scans or magnetic resonance imaging scans (MRIs). Three-dimensional (3D) ultrasound offers the opportunity to establish a 3D AAA model from which both the maximum diameter perpendicular to the centering of the abdominal aorta and a partial volume can be calculated. According to systems and methods described herein, 3D ultrasound can be used to measure aorta boundaries, such as estimate the AAA diameter perpendicular to the centering as well as the AAA volume. The systems and methods may perform 3D abdominal aorta segmentation based on a 3D vascular shape model and intensity model.

For example, in some implementations, a flexible 3D aorta model is applied to 3D echo data to provide image segmentation for structures of interest, such as the abdominal aorta (or other blood vessels) or other structures of interest (e.g., an aneurysm) based on information obtained via an ultrasound scanner. The flexible 3D aorta model is defined based on the human abdominal aorta, with possible variations integrated into the shape model. Fitting the flexible 3D aorta model to a new echo data set can be defined as minimizing a special energy function. In some implementations, the flexible 3D aorta model may be a defined segment. In other implementations, the flexible 3D aorta model may be open-ended (e.g., without length restrictions). The intensity model can also be defined by analyzing the ultrasound image brightness inside and outside the aorta structures.

Segmentation is the first step for quantitative analysis in AAA evaluation using 3D ultrasound imaging. With abdominal aorta segmentation complete, post processing steps, such as centerline extraction and maximum diameter calculations, can be easily determined.

Figure 1:
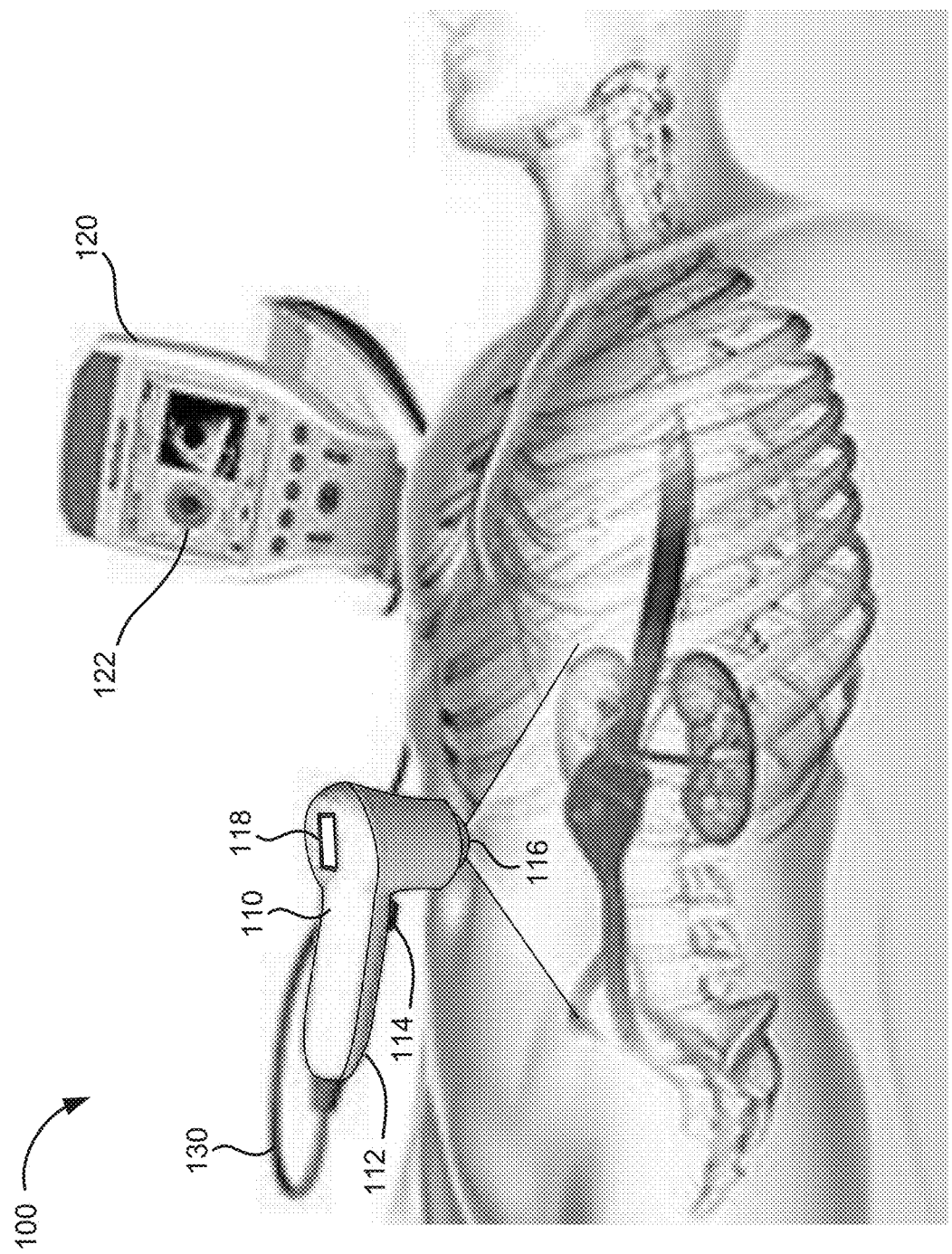
FIG. 1 is a schematic of a scanning system in which systems and methods described herein may be implemented.

FIG. 1 is a diagram illustrating an exemplary scanning system 100 consistent with an exemplary embodiment. Referring to FIG. 1, scanning system 100 includes a probe 110, a base unit 120, and a cable 130.

Probe 110 includes a handle portion 112 (also referred to as handle 112), a trigger 114 and a nose portion 116 (also referred to as dome or dome portion 116). Medical personnel may hold probe 110 via handle 112 and press trigger 114 to activate one or more ultrasound transceivers and transducers located in nose portion 116 to transmit ultrasound signals toward a patient's area of interest (e.g., a blood vessel, organ, joint, etc.). For example, as shown in FIG. 1, probe 110 may be positioned over the abdominal region of a patient and over a target vessel, such as the abdominal aorta to obtain an image of the abdominal aorta.

Handle 112 allows a user to move probe 110 relative to the patient's area of interest. As discussed above, trigger 114 initiates an ultrasound scan of a selected anatomical portion while dome 116 is in contact with a surface portion of a patient's body when the patient's area of interest is scanned. Dome 116 is typically formed of a material that provides an appropriate acoustical impedance match to the anatomical portion and/or permits ultrasound energy to be properly focused as the acoustical energy is projected into the anatomical portion. In some implementations, an acoustic gel or gel pads may be applied to a patient's skin over the region of interest (ROI) to provide an acoustical impedance match when dome 116 is placed against the patient's skin.

Dome 116 may enclose one or more ultrasound transceiver elements and one or more transducer elements (not shown in FIG. 1). The transceiver elements transmit ultrasound energy outwardly from the dome 116, and receive acoustic reflections or echoes generated by internal structures/tissue within the anatomical portion. The one or more ultrasound transducer elements may include a one-dimensional, or a two-dimensional array of piezoelectric elements that may be moved within dome 116 by a motor to provide different scan directions with respect the transmissions of ultrasound signals by the transceiver elements. Alternatively, the transducer elements may be stationary with respect to probe 110 so that the selected anatomical region may be scanned by selectively energizing the elements in the array.

In an exemplary implementation, the scanning protocol of system 100 is configurable. For example, scanning system 100 may be configured to increase the scanning plane density, increase the scanning line numbers or change the rotational scanning to a fan scanning method to capture three-dimensional (3D) image data, depending on the particular target organ of interest, size of the target organ of interest, etc., as described in more detail below.

In some implementations, probe 110 may include a directional indicator panel 118 that includes a number of arrows that may be illuminated for initial targeting and guiding a user to scan a vessel, organ or other structure within the ROI. For example, in some implementations, if the vessel, organ or structure is centered from placement of probe 110 placed against the dermal surface at a first location of a patient, the directional arrows may not be illuminated. However, if the vessel, organ or structure is off-center, an arrow or set of arrows may be illuminated to direct the user to reposition probe 110 at a second or subsequent dermal location of the patient. In other implementations, the directional indicators may be presented on display 122 of base unit 120.

The one or more transceivers located in probe 110 may include an inertial reference unit that includes an accelerometer and/or gyroscope positioned preferably within or adjacent to dome 116. The accelerometer may be operable to sense an acceleration of the transceiver, preferably relative to a coordinate system, while the gyroscope may be operable to sense an angular velocity of the transceiver relative to the same or another coordinate system. Accordingly, the gyroscope may be of a conventional configuration that employs dynamic elements, or may be an optoelectronic device, such as an optical ring gyroscope. In one embodiment, the accelerometer and the gyroscope may include a commonly packaged and/or solid-state device. In other embodiments, the accelerometer and/or the gyroscope may include commonly packaged micro-electromechanical system (MEMS) devices. In each case, the accelerometer and gyroscope cooperatively permit the determination of positional and/or angular changes relative to a known position that is proximate to an anatomical region of interest in the patient. Using these sensors (e.g., accelerometer, gyroscope, etc.) may help scanning system 100 reconstruct a 3D aorta vessel by combining scans at different locations, such as when the entire length of the aorta cannot be fully recovered in a single scan.

Probe 110 may communicate with base unit 120 via a wired connection, such as via cable 130. In other implementations, probe 110 may communicate with base unit 120 via a wireless connection (e.g., Bluetooth, WiFi, etc.). In each case, base unit 120 includes display 122 to allow a user to view processed results from an ultrasound scan, and/or to allow operational interaction with respect to the user during operation of probe 110. For example, display 122 may include an output display/screen, such as a liquid crystal display (LCD), light emitting diode (LED) based display, or other type of display that provides text and/or image data to a user. For example, display 122 may provide instructions for positioning probe 110 relative to the selected anatomical portion of the patient. Display 122 may also display two-dimensional or three-dimensional images of the selected anatomical region.

To scan a selected anatomical portion of a patient, dome 116 may be positioned against a surface portion of patient that is proximate to the anatomical portion to be scanned. The user actuates the transceiver by depressing trigger 114. In response, the transducer elements optionally position the transceiver, which transmits ultrasound signals into the body, and receives corresponding return echo signals that may be at least partially processed by the transceiver to generate an ultrasound image of the selected anatomical portion. In a particular embodiment, system 100 transmits ultrasound signals in a range that extends from approximately about two megahertz (MHz) to approximately 10 or more MHz (e.g., 18 MHz).

In one embodiment, probe 110 may be coupled to a base unit 120 that is configured to generate ultrasound energy at a predetermined frequency and/or pulse repetition rate and to transfer the ultrasound energy to the transceiver. Base unit 120 also includes one or more processors or processing logic configured to process reflected ultrasound energy that is received by the transceiver to produce an image of the scanned anatomical region.

In still another particular embodiment, probe 110 may be a self-contained device that includes a microprocessor positioned within the probe 110 and software associated with the microprocessor to operably control the transceiver, and to process the reflected ultrasound energy to generate the ultrasound image. Accordingly, a display on probe 110 may be used to display the generated image and/or to view other information associated with the operation of the transceiver. For example, the information may include alphanumeric data that indicates a preferred position of the transceiver prior to performing a series of scans. In other implementations, the transceiver may be coupled to a local or remotely-located general-purpose computer, such as a laptop or a desktop computer that includes software that at least partially controls the operation of the transceiver, and also includes software to process information transferred from the transceiver so that an image of the scanned anatomical region may be generated.

Figure 2:
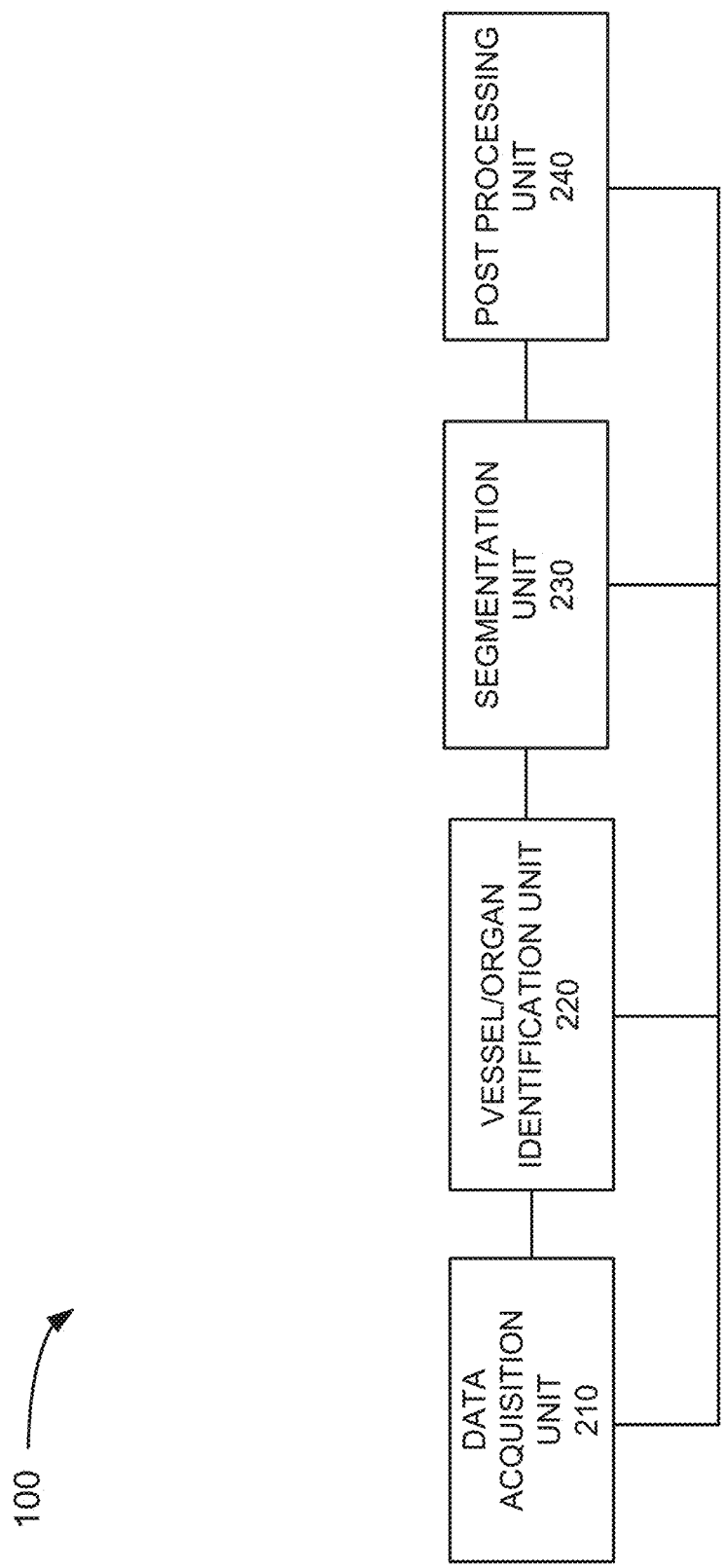
FIG. 2 illustrates an exemplary configuration of logic elements included in the scanning system of FIG. 1.

FIG. 2 is a block diagram of functional logic components implemented in system 100 in accordance with an exemplary implementation. Referring to FIG. 2, system 100 includes a data acquisition unit 210, a vessel/organ identification unit 220, a segmentation unit 230, and post-processing unit 240. In an exemplary implementation, data acquisition unit 210 may be part of probe 110 and the other functional units (e.g., vessel/organ identification unit 220, segmentation unit 230, and post-processing unit 240) may be implemented in base unit 120. In other implementations, the particular units and/or logic may be implemented by other devices, such as via computing devices or servers located externally with respect to both probe 110 and base unit 120 (e.g., accessible via a wireless connection to the Internet or to a local area network within a hospital, etc.). For example, probe 110 may transmit echo data and/or image data to a processing system via, for example, a wireless connection (e.g., WiFi or some other wireless protocol/technology) that is located remotely from probe 110 and base unit 120.

As described above, probe 110 may include one or more transceivers that produces ultrasound signals, receives echoes from the transmitted signals and generates B-mode image data based on the received echoes. In an exemplary implementation, data acquisition unit 210 obtains data associated with multiple scan planes corresponding to the region of interest in a patient. For example, probe 110 may receive echo data that is processed by data acquisition unit 210 to generate two-dimensional (2D) B-mode image data to determine a size of the abdominal aorta and/or the size of an aneurysm in abdominal aorta. In other implementations, probe 110 may receive echo data that is processed to generate three-dimensional (3D) image data that can be used to determine the size of the abdominal aorta.

Vessel/organ identification unit 220 may perform pre-processing of an image and detect if a vessel or organ is present within a region of interest based on, for example, differentiation of pixel intensity (e.g., as scanned and collected by data acquisition unit 210). As examples of pre-processing, vessel/organ identification unit 220 may apply noise reduction, adjust the aspect ratio of the raw B-mode image, and/or apply a scan conversion. As an example of vessel identification, in a 2D image, a blood carrying vessel may be identified as a dark region within an area of lighter-shaded pixels, where the lighter-shaded pixels typically represent body tissues. In another implementation, vessel/organ identification unit 220 may include artifact detection logic to detect particular structures adjacent the aorta, similar to that used in bladder scanning.

Segmentation unit 230 may receive data from data acquisition unit 210 and/or vessel/organ identification unit 220 and apply image processing using a 3D vascular shape model to segment the abdominal aorta. The 3D vascular shape model may include simulated 3D AAA shapes derived from human samples. An intensity model may include ultrasound image brightness information derived from human samples. In one implementation, segmentation unit 230 may apply a flexible 3D vascular shape model to a target 3D image. For example, as described in more detail below, segmentation unit 230 may fit a 3D vascular shape to a target image data set by minimizing one of several possible energy functions.

Post processing unit 240 includes logic to identify a size of an abdominal aorta that includes an aneurysm located in the abdominal aorta, as well as identify the size (e.g., diameter) and centerline of the aneurysm. For example, post processing unit 240 can provide a 3D reconstruction function to fully construct the aorta structure by combining all segmentation results associated with received echo data. In this manner, the measurement of the aorta diameter will be more accurate as compared to using conventional 2D imaging, as described in detail below.

The exemplary configuration illustrated in FIG. 2 is provided for simplicity. System 100 may include more or fewer logic units/devices than illustrated in FIG. 2. For example, system 100 may include multiple data acquisition units 210 and multiple processing units that process the received data. In addition, system 100 may include additional elements, such as communication interfaces (e.g., radio frequency transceivers) that transmit and receive information via external networks to aid in analyzing ultrasound signals to identify a target in a region of interest. Furthermore, while illustrations and descriptions herein primarily refer to blood vessel applications (e.g., identifying an abdominal aorta and/or an aneurism within the abdominal aorta), other embodiments may be applied to detecting boundaries of organs, such as the bladder, prostate/kidney boundary, thyroid, etc.

Figure 3A:
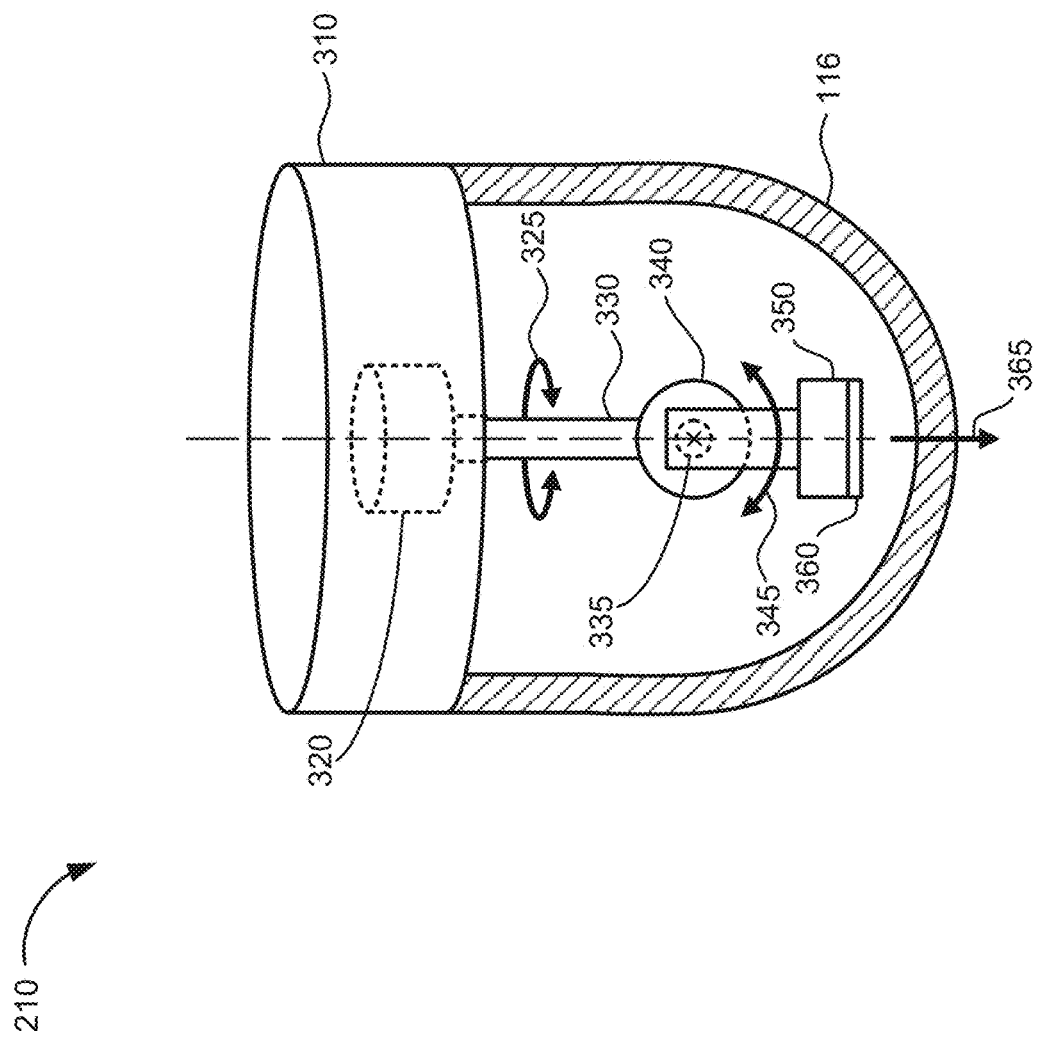
FIG. 3A illustrates a portion of the probe of FIG. 1 in accordance with an exemplary implementation.

FIG. 3A illustrates an exemplary data acquisition unit 210 used to obtain ultrasound image data. Referring to FIG. 3A, data acquisition unit 210 may include a single transducer element coupled to two rotational motors. In this implementation, ultrasound probe 110 may include a base 310 connected to dome 116, a theta motor 320, a spindle 330, a phi motor 340, and a transducer bucket 350 with a transducer 360. Theta motor 320, phi motor 340, transducer bucket 350 and/or transducer 360 may include wired or wireless electrical connections that electrically connect theta motor 320, phi motor 340, transducer bucket 350 and/or transducer 360 to base unit 120 via cable 130 (not shown in FIG. 3A).

Base 310 may house theta motor 320 and provide structural support to ultrasound probe 110. Base 310 may connect to dome 116 (connection not shown in FIG. 3A) and may form a seal with dome 116 to protect the components of ultrasound probe 110 from the external environment. Theta motor 320 may rotate spindle 330 with respect to base 310 in a longitudinal direction with respect to transducer 360, by rotating around a vertical axis referred to herein as a theta ($\theta$) rotational axis 325. Spindle 330 may terminate in a shaft 335 and phi motor 340 may be mounted onto shaft 335. Phi motor 340 may rotate around an axis orthogonal to the theta rotational axis 325 around a horizontal axis referred to herein as a phi ($\phi$) rotational axis 345. Transducer bucket 350 may be mounted to phi motor 340 and may move with phi motor 340.

Transducer 360 may be mounted to transducer bucket 350. Transducer 360 may include a piezoelectric transducer, a capacitive transducer, and/or another type of ultrasound transducer. Transducer 360, along with transceiver circuitry associated with transducer 360, may convert electrical signals to ultrasound signals at a particular ultrasound frequency or range of ultrasound frequencies, may receive reflected ultrasound signals (e.g., echoes, etc.), and may convert the received ultrasound signals to electrical signals. Transducer 360 may transmit and receive ultrasound signals in a signal direction 365 that is substantially perpendicular to the surface of transducer 360.

Signal direction 365 may be controlled by the movement of phi motor 340 and the orientation of phi motor 340 may be controlled by theta motor 320. For example, phi motor 340 may rotate back and forth across an angle that is less than 180 degrees (e.g., 120 degrees) to generate ultrasound image data for a particular plane and theta motor 320 may rotate to particular positions to obtain ultrasound image data for different planes.

In an aiming mode, theta motor 320 may remain stationary while phi motor 340 rotates back and forth to obtain ultrasound image data for a particular aiming plane. In the aiming mode, theta motor 320 may move back and forth between multiple aiming planes and phi motor 340 may rotate back and forth to obtain ultrasound image data. As an example, theta motor 320 may move between two orthogonal planes while the aiming mode is selected. As another example, theta motor 320 may sequentially rotate through three planes offset by 120 degrees to each other during the aiming mode.

In a 3D scan mode, theta motor 320 may cycle through a set of planes (or "slices") one or more times to obtain a full 3D scan of an area of interest. Higher scan resolution may be obtained by using more scanning planes. Thus, in contrast with a conventional 12-plane scan, implementations described herein may use a set of 48 planes to achieve resolutions that support the shape fitting methods described herein. In other implementation, more or fewer planes than 48 may be used. In each particular plane of the set of planes, phi motor 340 may rotate to obtain ultrasound image data for the particular plane. The movement of theta motor 320 and phi motor 340 may be interlaced in the 3D scan motor. For example, the movement of phi motor 340 in a first direction may be followed by a movement of theta motor 320 from a first plane to a second plane, followed by the movement of phi motor 340 in a second direction opposite to the first direction, followed by movement of theta motor 320 from the second plane to a third plane, etc. Such interlaced movement may enable ultrasound probe 110 to obtain smooth continuous volume scanning as well as improve the rate at which the scan data is obtained.

Figure 3B:
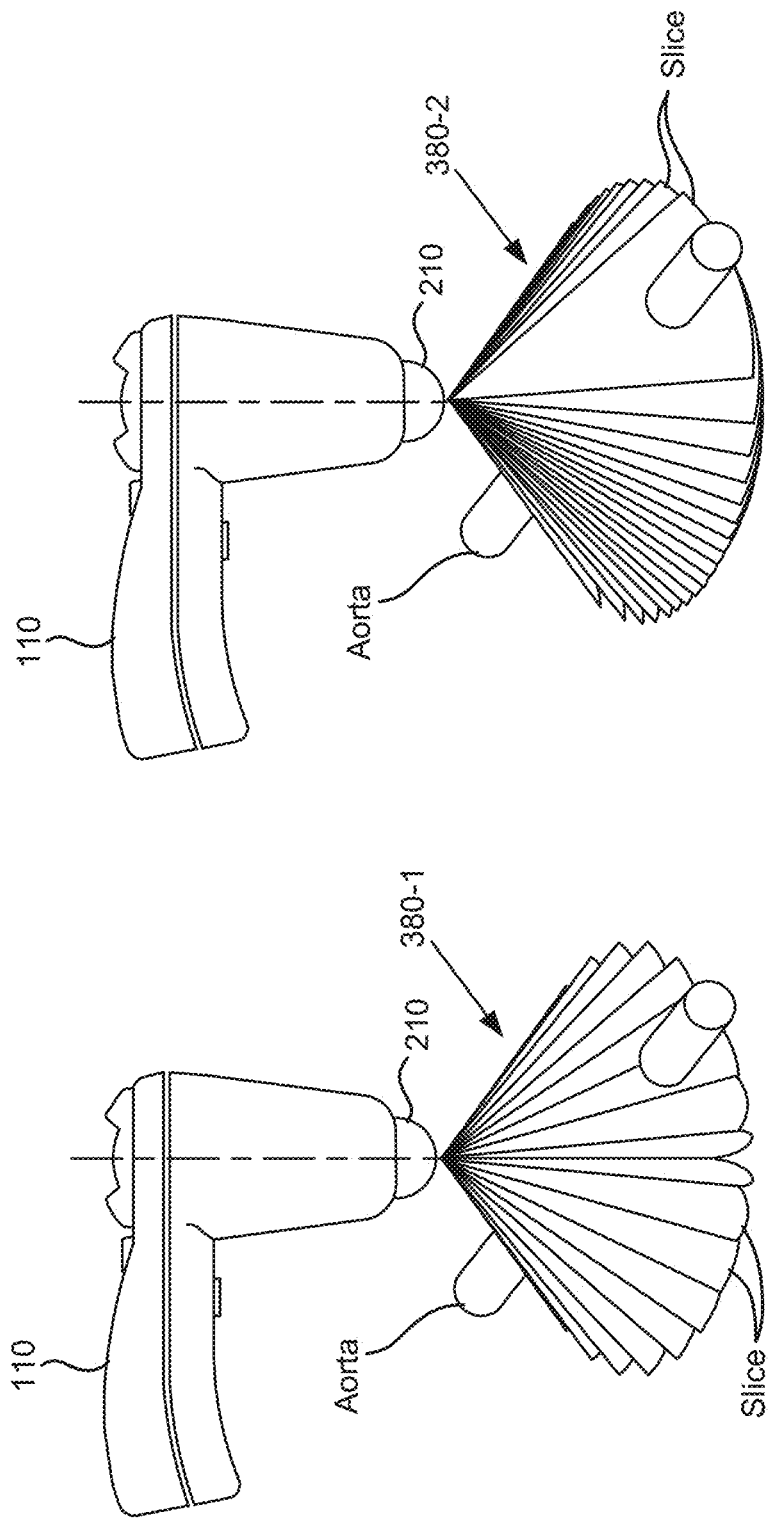
FIG. 3B illustrates capturing echo data associated with B-mode scanning planes using the probe of FIG. 1.

In addition, theta motor 320 and phi motor 340 can be configured to increase the scanning line numbers, change the rotational scanning to a "fan scanning" method, when the entire aorta cannot be captured via a first set of scan planes and a first set of reconstructed slices, as illustrated in FIG. 3B. For example, FIG. 3B illustrates a scenario in which an initial ultrasound cone 380-1 from a rotational scan did not capture the complete length of the aorta based on the length of the aorta. In this case, theta motor 320 and phi motor 340 can modify the rotational angles associated with transducer 360 to capture and evaluate vascular structures quantitatively based on cross-sectional slices to capture additional data so that the entire aorta structure can be analyzed. The subsequent ultrasound cone 380-2 from this fan scanning may capture a larger portion of the vascular structure than ultrasound cone 380-1.

In another implementation, image acquisition unit 210 may capture additional data (e.g., beyond the scope of a single ultrasound cone 380-1) by stitching together scans from multiple ultrasound cones to acquire a larger target image. FIG. 3C is a schematic of probe 110 collecting data using two ultrasound cones 380-3 and 380-4 spanning a target image (e.g., a patient's abdominal aorta). Images from ultrasound cones 380-3 and 380-4 may be obtained sequentially, and image acquisition unit 210 may stitch together or combine images/views from multiple slices of each ultrasound cone to construct a complete view of the target image.

Figure 3D:
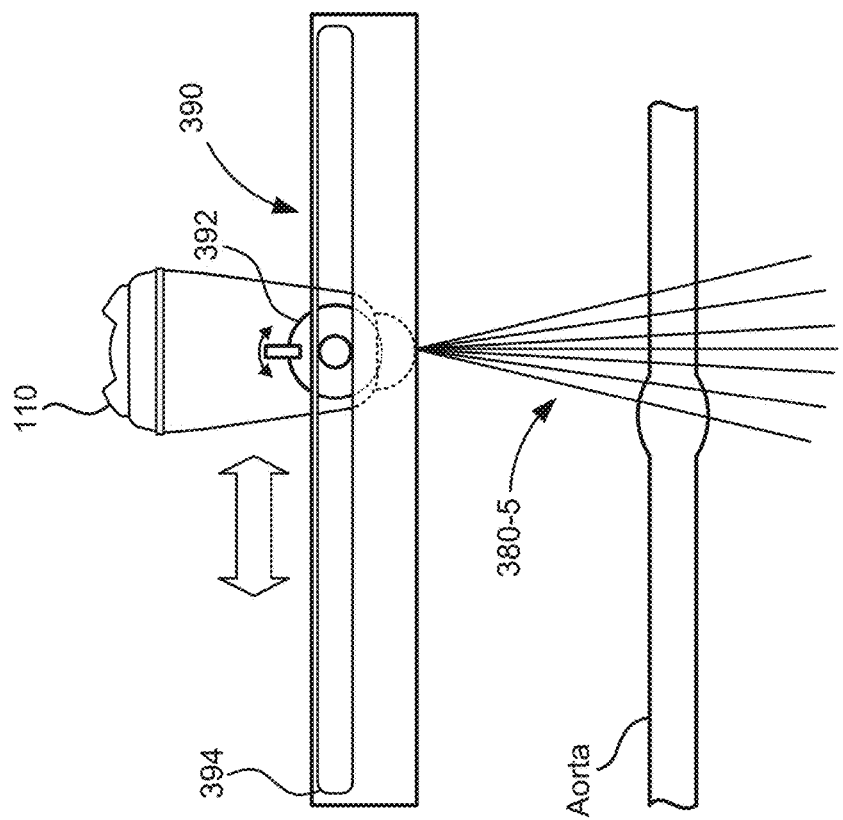
FIG. 3D illustrates capturing echo data using a position tracking system and the probe of FIG. 1.
Figure 3C:
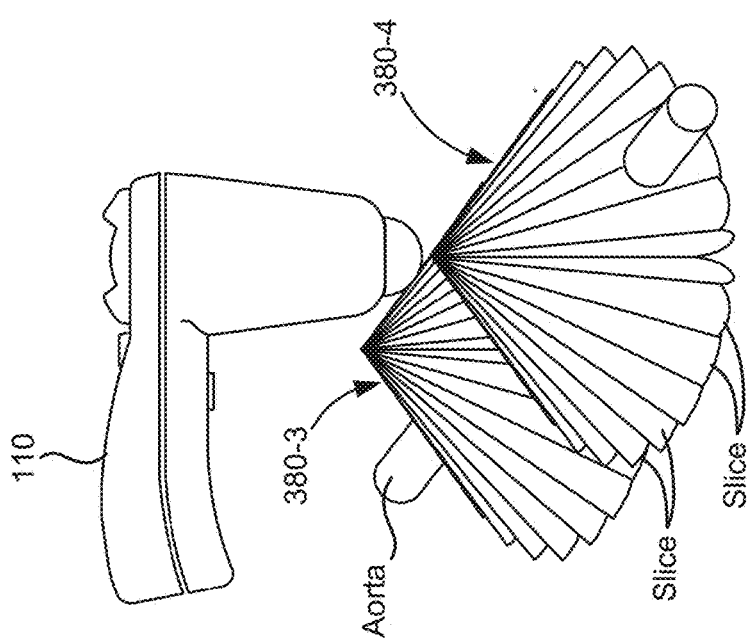
FIG. 3C illustrates capturing echo data associated with two ultrasound cones using the probe of FIG. 1.

As shown in FIG. 3D, in still another implementation, image acquisition unit 210 may use a tracking system 390 to control and/or monitor a relative position of a probe, such as probe 110. FIG. 3D provides a simplified side-view illustration of probe 110 mounted on tracking system 390. Tracking system may include a rotatable probe holder 392 mounted within a track 394. According to one embodiment, tracking system 390 may move probe 110 along track 394, monitoring a track position and rotation of probe holder 392 as an ultrasound cone 380-5 moves over an area of interest (e.g., above a patient's abdominal aorta). Tracking system 390 may monitor the location of probe 110 along track 394 using mechanical index tracking, electromagnetic tracking, optical tracking, or other sensors. In another implementation, an articulated arm may be used in place of track 394. Using tracking system 390, images from ultrasound cone 380-5 may be stitched together or combined based on the relative position/orientation of probe 110 to construct a complete view of a target image.

Figure 3E:
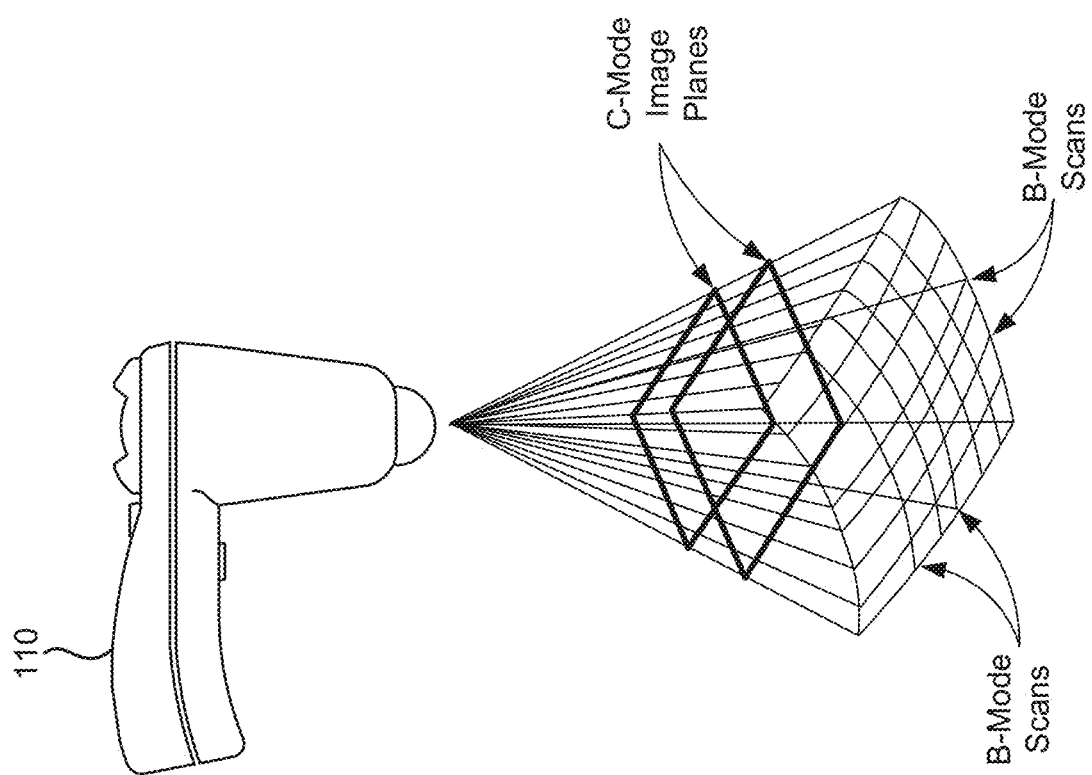
FIG. 3E illustrates capturing echo data associated with C-mode scanning planes using the probe of FIG. 1.

FIG. 3E provides a simplified illustration of C-mode image planes. C-mode images may generally include a representation oriented perpendicular to typical B-mode scan planes, for example. In one implementation, a C-mode image may include a cross-sectional image generated from ultrasound data of rotational scan planes at a particular depth. Thus, data acquisition unit 210 may use image data from different depths in each B-mode scan plane (or slice) to generate a C-mode image. The C-mode may be more representative of a portion of the abdominal aorta than the actual whole of the length of the aorta. The targeting image may be more of a binary image showing the lines and spaces that are inside the aorta versus those that are outside of the aorta. The C-mode acquired projection image can yield abdominal aorta information not confined to simply one a single plane parallel to the transducer surface, but multiple planes denoted as C-mode image planes.

Systems and methods described herein are described primarily in the context of image data obtained from an electro-mechanical probe performing rotational scanning. However, in other implementations, other types of probes may be used. For example, a matrix probe, a freehand magnetic probe, or a freehand optical probe may also be used to obtain 3D image data.

Figure 4:
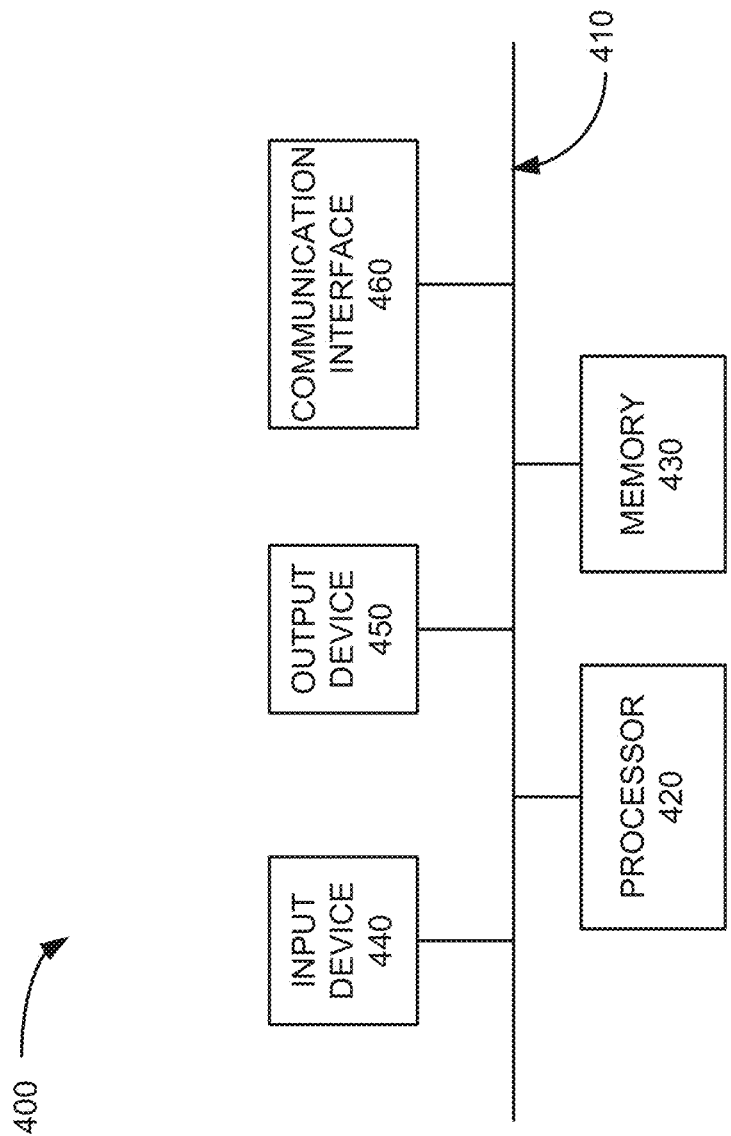
FIG. 4 illustrates an exemplary configuration of components included in one or more of the elements of FIG. 1 and/or FIG. 2.

FIG. 4 illustrates an exemplary configuration of a device 400. Device 400 may correspond to, for example, a component of data acquisition unit 210, vessel/organ identification unit 220, segmentation unit 230, and/or post processing unit 240. Device 400 may also correspond to elements in FIG. 1, such as base unit 120. Referring to FIG. 4, device 400 may include bus 410, processor 420, memory 430, input device 440, output device 450 and communication interface 460. Bus 410 may include a path that permits communication among the elements of device 400.

Processor 420 may include one or more processors, microprocessors, or processing logic that may interpret and execute instructions. Memory 430 may include a random access memory (RAM) or another type of dynamic storage device that may store information and instructions for execution by processor 420. Memory 430 may also include a read only memory (ROM) device or another type of static storage device that may store static information and instructions for use by processor 420. Memory 430 may further include a solid state drive (SDD). Memory 430 may also include a magnetic and/or optical recording medium (e.g., a hard disk) and its corresponding drive.

Input device 440 may include a mechanism that permits a user to input information to device 400, such as a keyboard, a keypad, a mouse, a pen, a microphone, a touch screen, voice recognition and/or biometric mechanisms, etc. Output device 450 may include a mechanism that outputs information to the user, including a display (e.g., a liquid crystal display (LCD)), a printer, a speaker, etc. In some implementations, a touch screen display may act as both an input device and an output device.

Communication interface 460 may include one or more transceivers that device 400 uses to communicate with other devices via wired, wireless or optical mechanisms. For example, communication interface 460 may include one or more radio frequency (RF) transmitters, receivers and/or transceivers and one or more antennas for transmitting and receiving RF data via a network. Communication interface 460 may also include a modem or an Ethernet interface to a LAN or other mechanisms for communicating with elements in a network.

The exemplary configuration illustrated in FIG. 4 is provided for simplicity. It should be understood that device 400 may include more or fewer devices than illustrated in FIG. 4. In an exemplary implementation, device 400 performs operations in response to processor 420 executing sequences of instructions contained in a computer-readable medium, such as memory 430. A computer-readable medium may be defined as a physical or logical memory device. The software instructions may be read into memory 430 from another computer-readable medium (e.g., a hard disk drive (HDD), SSD, etc.), or from another device via communication interface 560. Alternatively, hard-wired circuitry, such as application specific integrated circuits (ASICs), field programmable gate arrays (FPGAs), etc., may be used in place of or in combination with software instructions to implement processes consistent with the implementations described herein. Thus, implementations described herein are not limited to any specific combination of hardware circuitry and software.

Referring again to FIG. 2, segmentation unit 230 may receive data from data acquisition unit 210 and/or vessel/organ identification unit 220 and analyze the data using 3D abdominal aorta segmentation based on a 3D vascular shape model and intensity model. Segmentation unit 230 may then provide the identified shape to post processing unit 240 for centerline extraction and maximum diameter measurement. In contrast with previous ultrasound based segmentation methods that analyze data on a pixel-by-pixel basis, systems and methods based on the 3D shape model described herein are more resilient to ultrasound noise and other artifacts. The systems and methods can also provide a more reliable and accurate diameter measurement method based on the resultant 3D structure.

Figure 5:
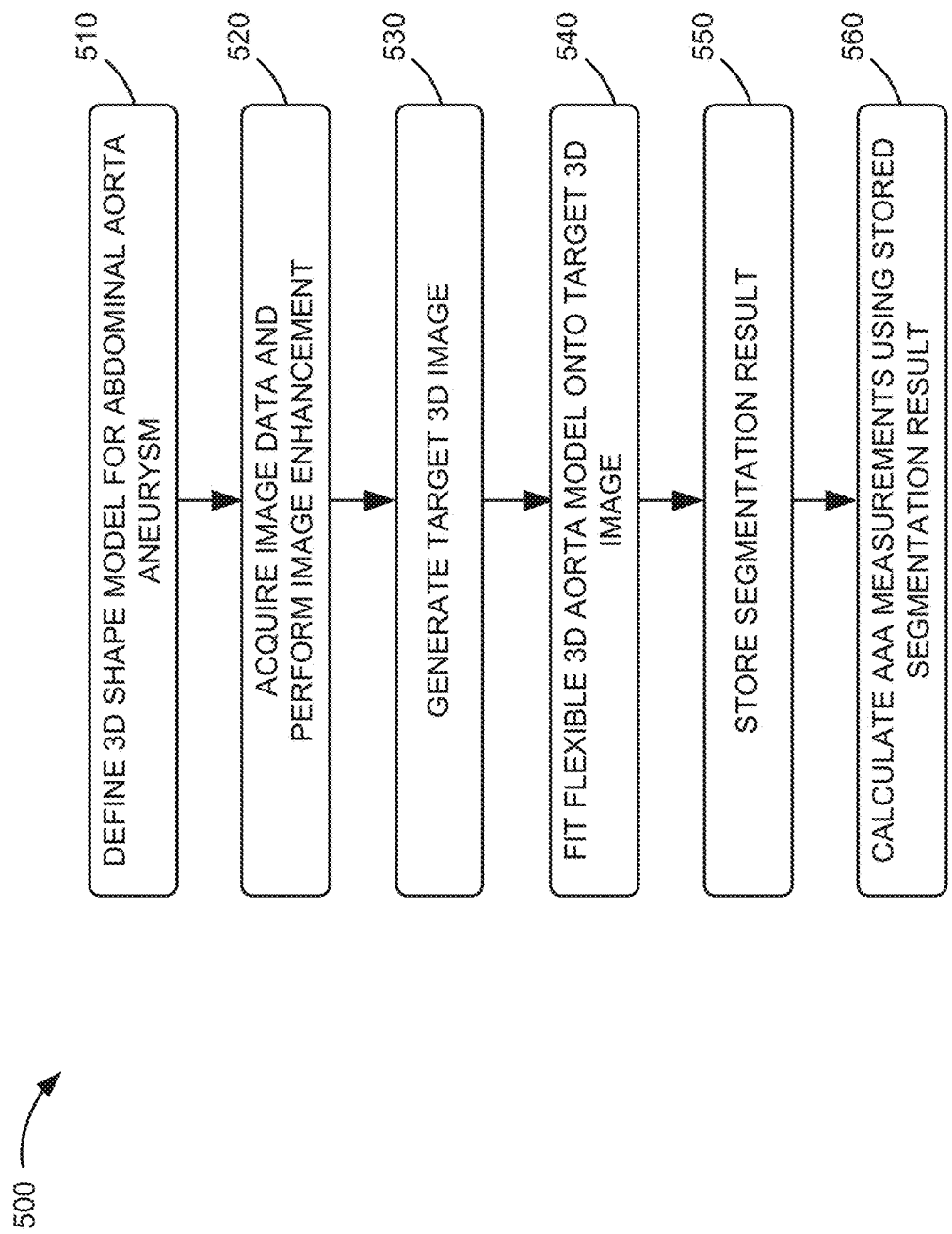
FIG. 5 is a flow diagram associated with measuring an abdominal aorta aneurism in accordance with an exemplary implementation.

FIG. 5 is a flow diagram illustrating exemplary processing 500 associated with identifying a target of interest, as well as identifying parameters or elements associated with the target of interest. Processing may begin with a user operating probe 110 to scan a target/region of interest. In this example, assume that the target is the abdominal aorta. It should be understood that features described herein may be used to identify other vessels, organs or structures within the body.

In an exemplary implementation, a 3D shape model may be defined for an abdominal aorta aneurysm (block 510). Generally, according to an exemplary implementation, the 3D vascular shape model can be used to represent a patient's real aorta for quantitative analysis purposes. The simulated 3D shape model may be defined based on data from multiple human abdominal aortas. Possible variations can then be integrated into the shape model. For example, as shown in FIG. 6A-6F, a simulated 3D AAA shape model may be developed based on human abdominal aorta characteristics.

Generally, the 3D AAA shapes in FIGS. 6A-6F may include a 3D tubes 602 and/or 3D balls 604 in combination representing an aneurysm.

Figure 6C:
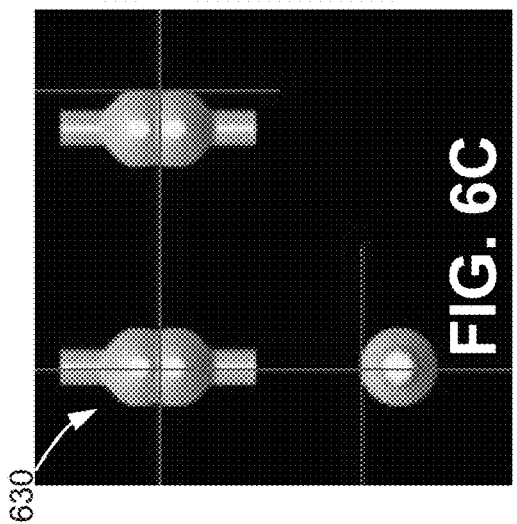
FIGS. 6A-6F illustrate simulated aorta data sets that can be used for a 3D shape model in accordance with the process of FIG. 5.
Figure 6F:
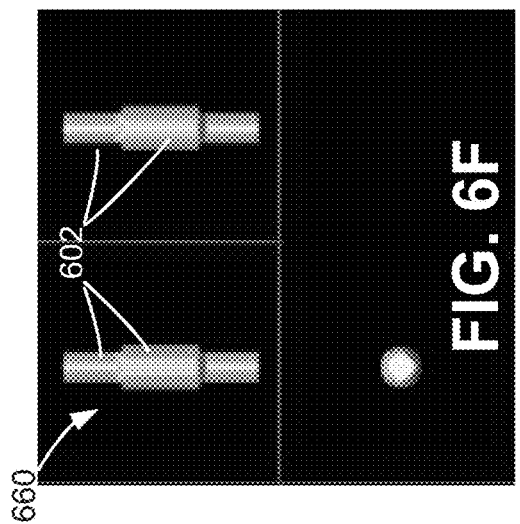
Figure 6B:
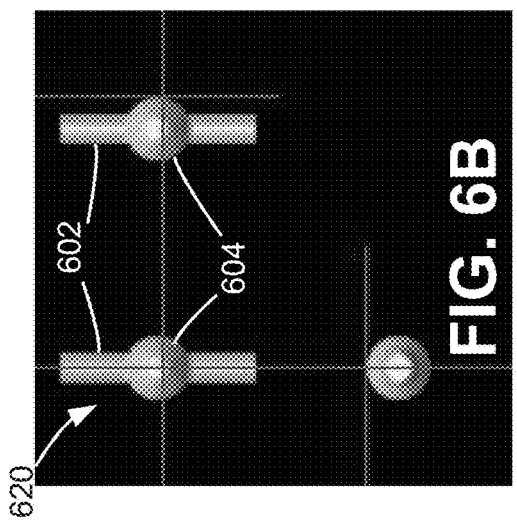
Figure 6E:
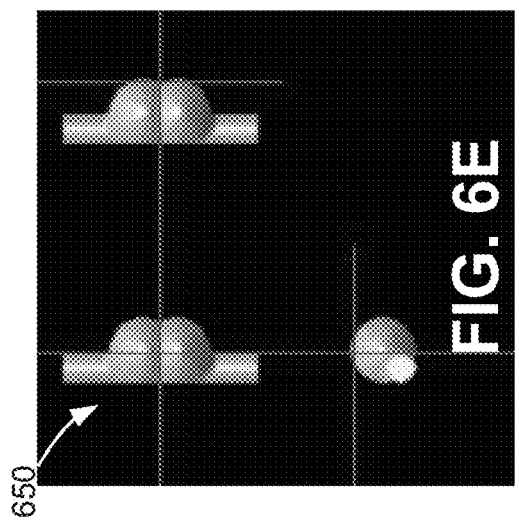
Figure 6A:
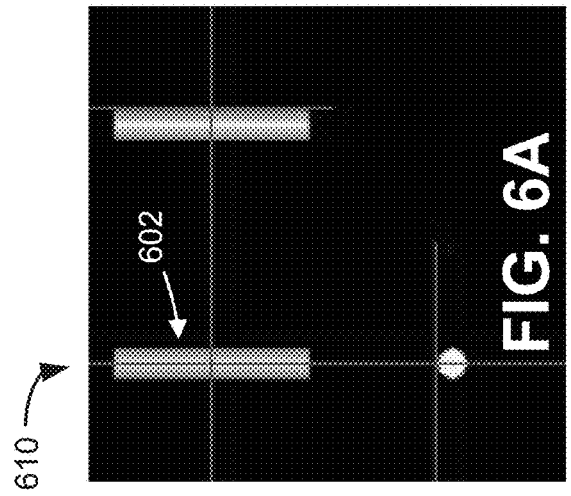
Figure 6D:
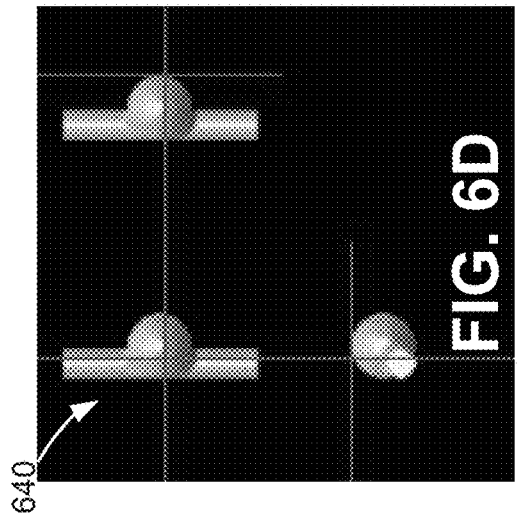

FIGS. 6A-6F represent six simulated 3D data sets that may be used for a flexible shape model. Each 3D data set includes a top view (anterior-posterior, illustrated in the upper left frame), side view (transverse, illustrated in the upper right frame), and end view (illustrated in the lower left frame) of a simulated AAA structure. FIG. 6A represents a simulation shape 610 with a normal aorta having no aneurysm. FIG. 6B represents a simulation shape 620 with an aorta having a spherical aneurysm along a centerline of the aorta. FIG. 6C represents a simulation shape 630 with an aorta having a double-spherical aneurysm along the centerline of the aorta. FIG. 6D represents a simulation shape 640 with an aorta having a spherical aneurysm off-center from a centerline of the aorta. FIG. 6E represents a simulation shape 650 with an aorta having a double-spherical aneurysm off-center from a centerline of the aorta. FIG. 6F represents a simulation shape 660 with an aorta having a tube-shaped aneurysm. In the model, tube diameters can be different for each tube, and tube diameters can be different in different tubes. Each of simulation shapes 610-660 may be derived from patient data (e.g., ultrasound data, CT scan data, MRI data, etc.) of normal and AAA conditions. Furthermore, ball diameters can be different in different tubes; and each ball can be a regular (e.g., spherical) shape or elongated. While six simulation shapes 610-660 are shown in FIGS. 6A-6F, in other implementations more or fewer simulation shapes may be used for the flexible shape model.

Figure 7A:
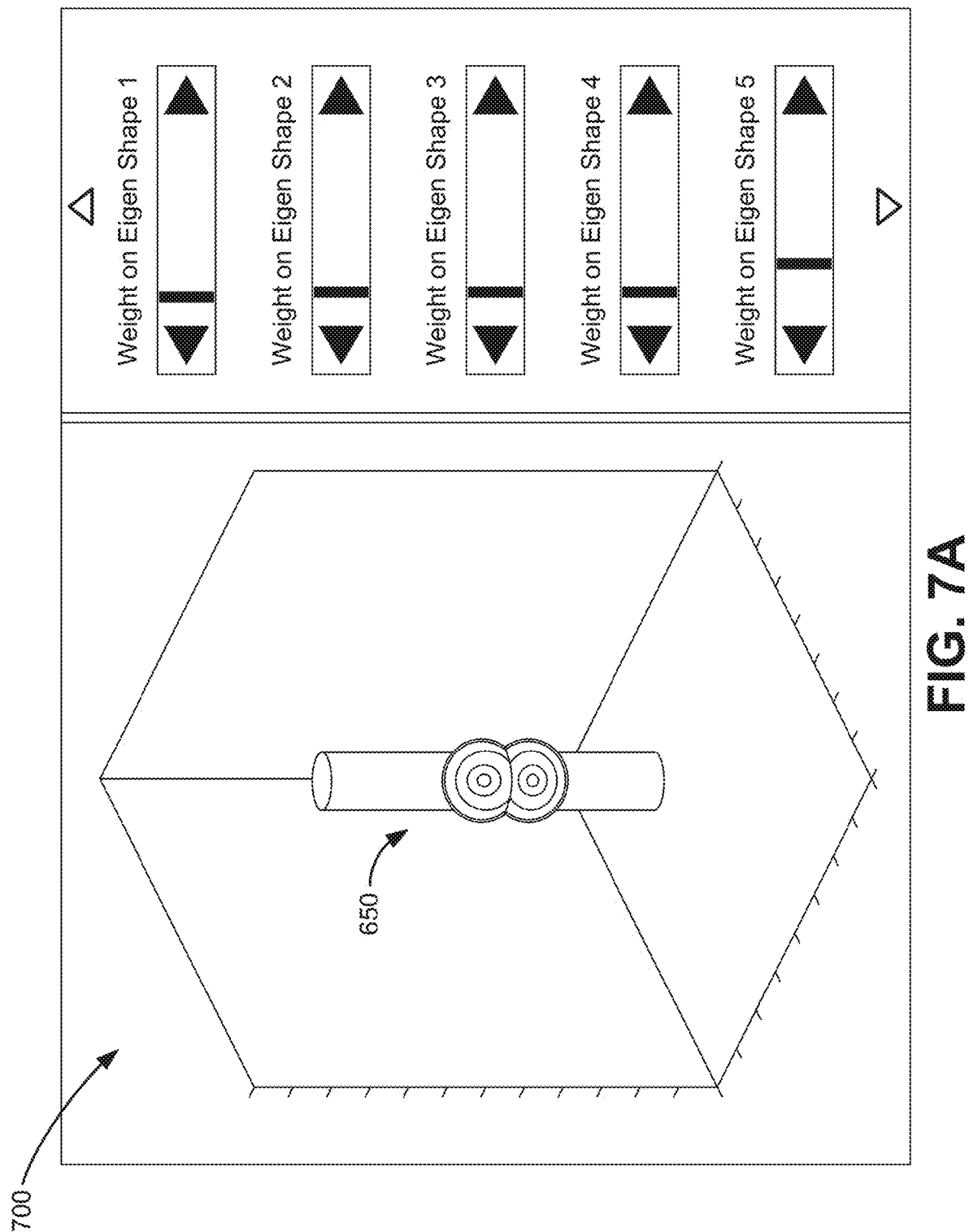
FIGS. 7A and 7B illustrate variations for a 3D shape model in accordance with the process of FIG. 5.
Figure 7B:
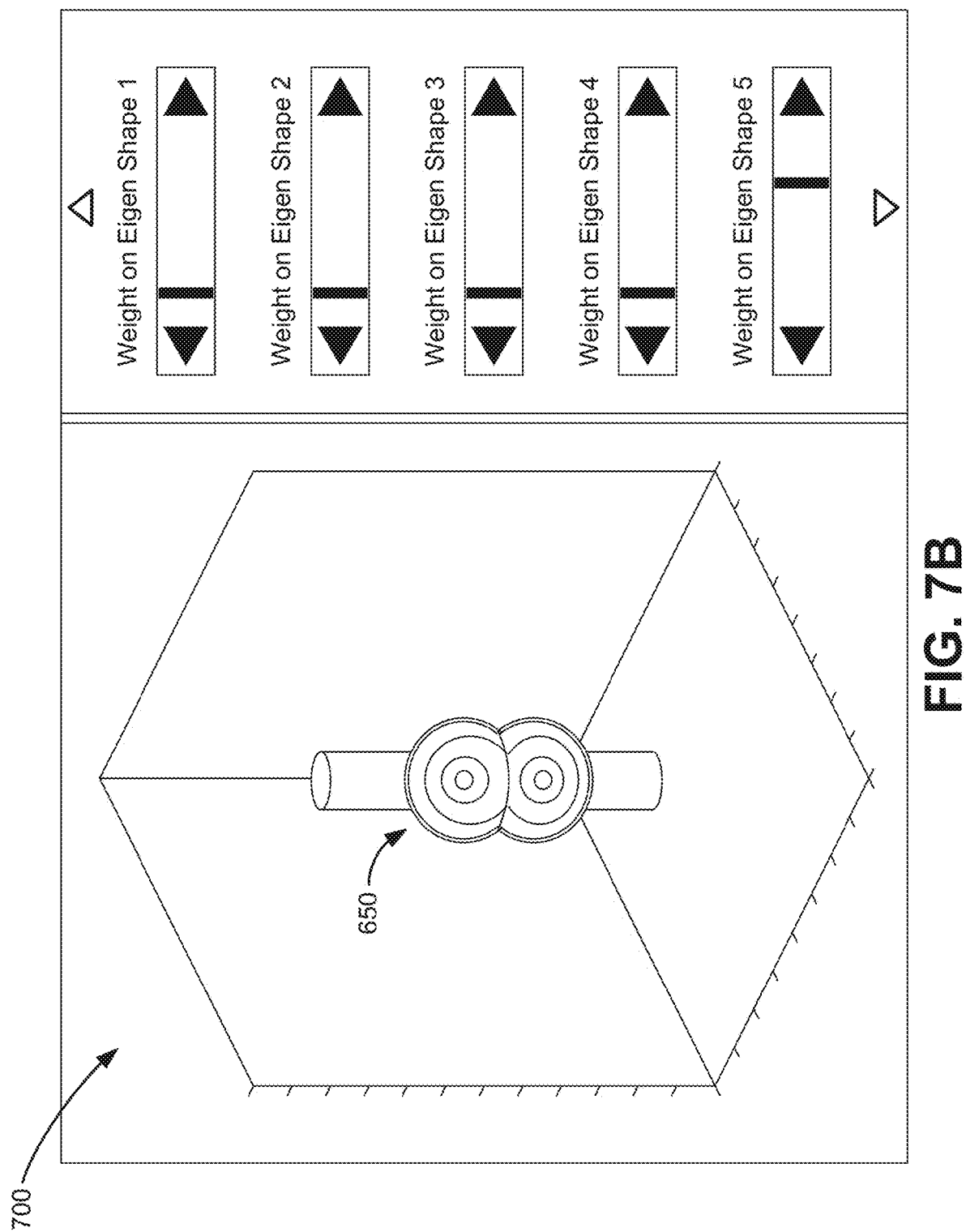

FIGS. 7A and 7B provide a simplified illustration a flexible shape model 700. More particularly, FIGS. 7A and 7B illustrate how a simulation shape (e.g., simulation shape 650) may be morphed for shape fitting analysis. Other simulation shapes (e.g., 610-640 and 660) may be modified or modified in a similar manner. In the example of FIGS. 7A and 7B, the weighted value of a double-spherical aneurysm off-center from a centerline (e.g., simulation shape 650, corresponding to Eigen Shape 5 of FIGS. 7A and 7B) is increased from a relatively small weight in FIG. 7A to a larger weight in FIG. 7B (as illustrated via the slide bar located on the right side of FIGS. 7A and 7B. According to an exemplary implementation, the flexible shape model can "learn" from the training patterns of simulation shapes 610-660. The flexible shape model may provide a flexible representation without using specific contours or a mesh. The flexible 3D shape model is thus more resistant to noise or shadow than conventional techniques in 2D space. While FIGS. 7A and 7B show flexible shape model 700 that may be manually adjusted using slide bars. In other implementations, flexible shape model 700 may be selected/adjusted using a processor (e.g., processor 420) in probe 110 or base unit 120.

Referring back to FIG. 5, image data of a patient may be acquired and image enhancement applied (block 520). For example, a user may press trigger 114 and the transceiver (e.g., associated with transducer 360) included in probe 110 transmits ultrasound signals and acquires B-mode data associated with echo signals received by probe 110. In one implementation, data acquisition unit 210 may transmit ultrasound signals on 12 different planes through the abdominal aorta and generate 12 B-mode images corresponding to the 12 different planes. In this implementation, the data may correspond to 2D image data. In other implementations, data acquisition unit 210 may generate 3D image data. For example, as discussed above with respect to FIGS. 3A-3D, data acquisition unit 210 may perform interlaced scanning to generate 3D images to capture the entire aorta structure. In each case, the number of transmitted ultrasound signals/scan planes may vary based on the particular implementation.

Probe 110 or base unit 120 may also apply a noise reduction process to the ultrasound image data. For example, data acquisition unit 210 may receive a B-mode ultrasound image from probe 110 and apply noise reduction and/or other pre-processing techniques to remove speckle and background noise from the image. In some embodiments, the aspect ratio of the raw B-mode image can be adjusted through a resizing process to compensate for differences between axial and lateral resolution. In other implementations, such as when performing an abdominal aorta scanning application, a scan conversion and/or machine learning can also be applied to make the abdominal aorta shape closer to the expected or actual shape of an abdominal aorta (e.g., elongated as opposed to round).

Figure 8A:
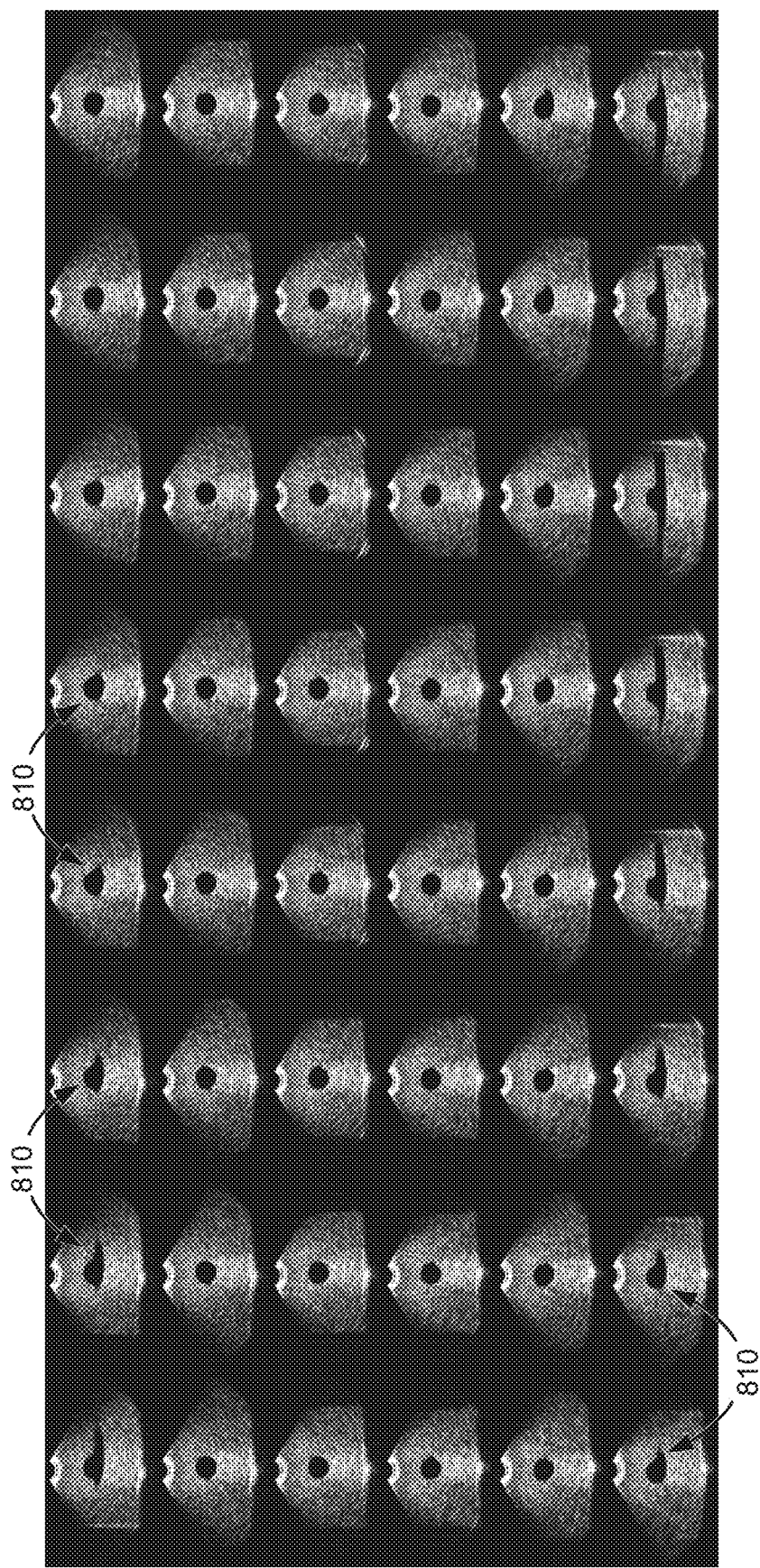
FIG. 8A is an illustration of a 48-plane rotational scan for an abdominal aorta phantom.

Base unit 120 (e.g., vessel/organ identification unit 220) may detect a region of interest, such as detect a concentration of dark pixels within the ultrasound image. The concentration of dark pixels typically corresponds to the lumen of the abdominal aorta, which carries the blood through the abdominal aorta. For example, FIG. 8A illustrates a series of images from a 48-slice rotational scan of a AAA phantom that may be generated by data acquisition unit 210, which shows the phantom 810 as a concentration of dark pixels in the center of each B-mode scan plane. While phantom 810 is used for purposes of illustration, systems and methods described herein apply equally well to human aorta/tissues. Vessel/organ identification unit 220 may identify the area of dark pixels as the lumen. In another implementation, base unit 120 may include a user interface (e.g., a touch screen, tablet, mouse, etc.) to allow an operator to indicate or select a vessel or organ of interest, such as selecting the abdominal aorta lumen from one of the scan images via display 122.

Figure 8B:
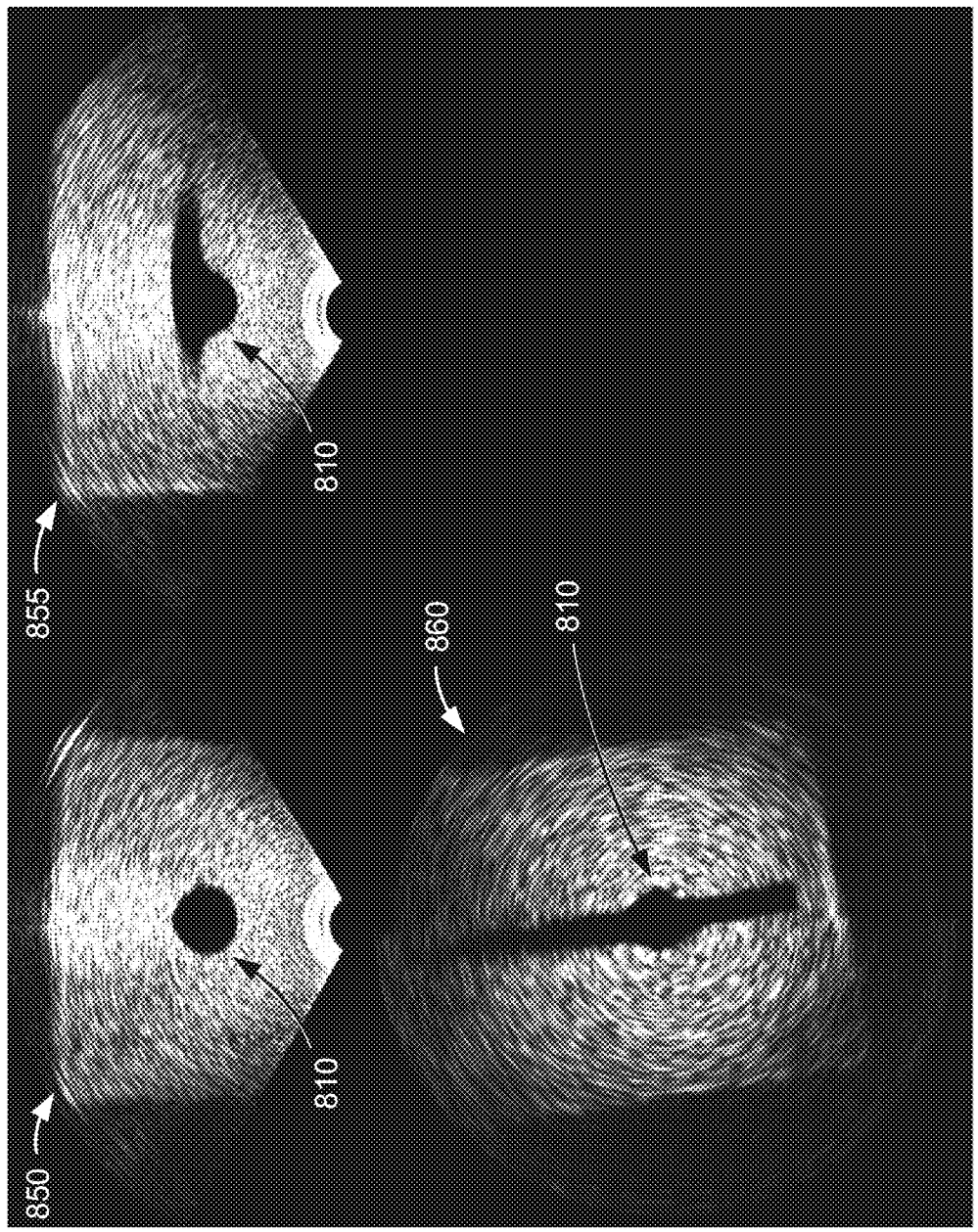
FIG. 8B is an illustration of interpolation B-mode and C-mode images from the rotational scan images of FIG. 8A.

Still referring to FIG. 5, once the abdominal aorta lumen is identified, vessel/organ identification unit 220 may generate a 3D target image of the abdominal aorta (block 530). For example, 3D image data may be compiled based on B-mode scans. In one implementation, the rotational scan B-mode images from FIG. 8A may be used to generate 3D image data (e.g., with top, side, and end views) shown in FIG. 8B. FIG. 8B includes exemplary images of a cross sectional end view 850, a longitudinal section 855, and a C-mode representation 860 of the AAA phantom 810 of FIG. 8A. The renderings of phantom 810 in sections 850, 855, and 860 may be used together as a target 3D image data set 820 to be matched by the flexible shape model (e.g., flexible shape model 700).

Figure 9C:
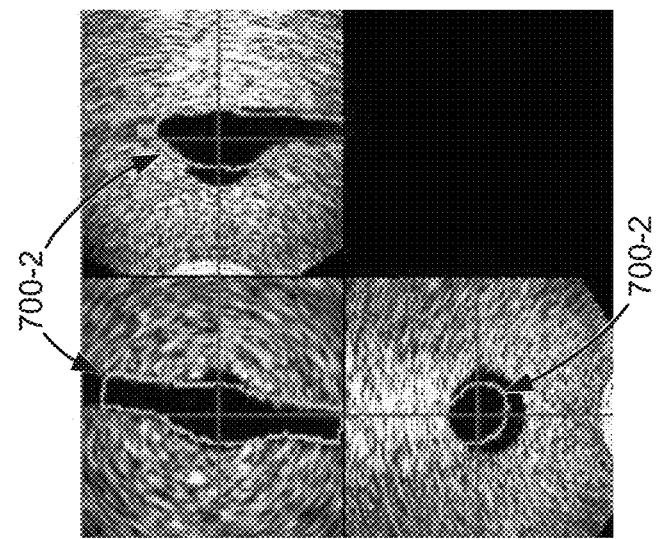
FIGS. 9A-9C illustrate applying a flexible 3D shape model to a target data set in accordance with an exemplary implementation.
Figure 9B:
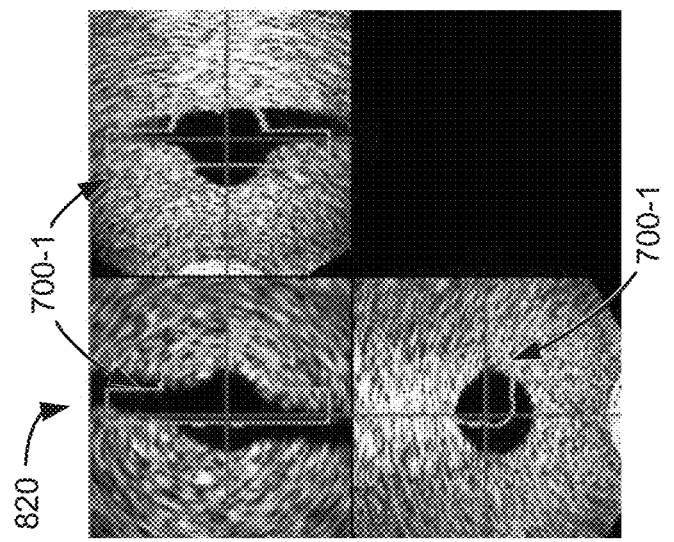
Figure 9A:
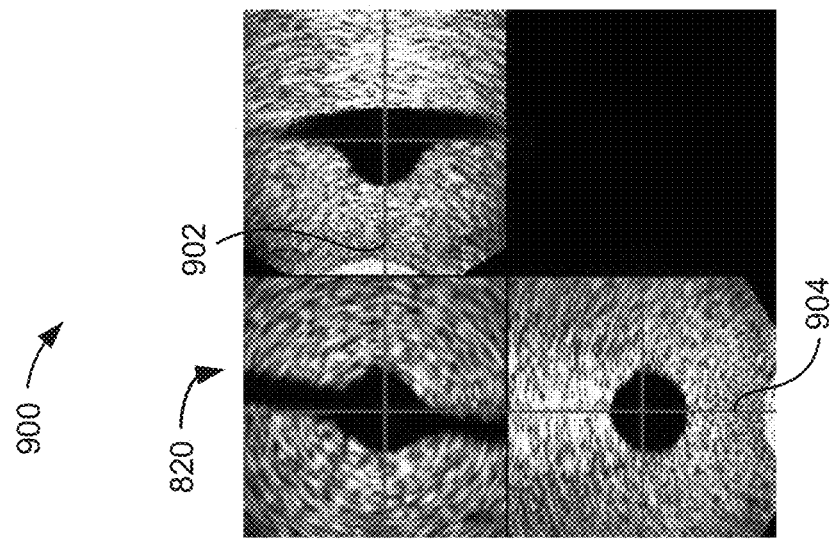

As further shown in FIG. 5, the flexible 3D aorta model may be fit onto the target 3D image (block 540). For example, segmentation unit 230 may overlay flexible shape model 700 onto target 3D image data set 820 to determine a best fit. FIGS. 9A-9C illustrate a shape fitting procedure 900. FIG. 9A is an illustration of portions of sections 850, 855, and 860 from target 3D image data set 820 shown without overlays and aligned along center lines 902, 904. FIG. 9B is an illustration of an initial configuration of flexible shape model 700-1 overlaid on target 3D image data set 820.

In the example of FIG. 9B, simulation shape 650 (e.g., a double-spherical aneurysm off-center from a centerline) may be initially selected as a starting image. Selection of the initial simulation shape may be performed by segmentation unit 230, provided by an operator (e.g., using display 122), or included as a default selection. In one implementation, fitting flexible shape model 700 to target 3D image data set 820 can be defined as minimizing an energy function.

One or more different approaches to minimizing an energy functions may be used to fit shape model 700 to a target 3D image data set (e.g., target image data set 820). For example, resilient backpropagation (rprop) is a learning heuristic for supervised learning in feedforward artificial neural networks. Rprop takes into account only the sign of the partial derivative over all patterns (not the magnitude), and acts independently on each "weight." For each weight, if there was a sign change of the partial derivative of the total error function compared to the last iteration, the update value for that weight is multiplied by a factor η−, where η−<1. If the last iteration produced the same sign, the update value is multiplied by a factor of η+, where η+>1. The update values are calculated for each weight in the above manner, and finally each weight is changed by its own update value, in the opposite direction of that weight's partial derivative, so as to minimize the total error function. In one implementation, η+ is empirically set to 1.1 and η− to 0.9.

An energy function that may be used to fit shape model 700 to a target 3D image data set is a data-driven statistical shape model. The data-driven statistical shape model may be more robust to the initialization and robust to noise during the segmentation task. Given a set of aligned training shapes $\{\varphi_i\}i=1 \ldots N$, each of the shapes can be represented by their corresponding shape vector $\{\alpha_i\}i=1 \ldots N$. In this notation, the goal of statistical shape learning is to infer a statistical distribution $P(\alpha)$ from the training samples.

Figure 10C:
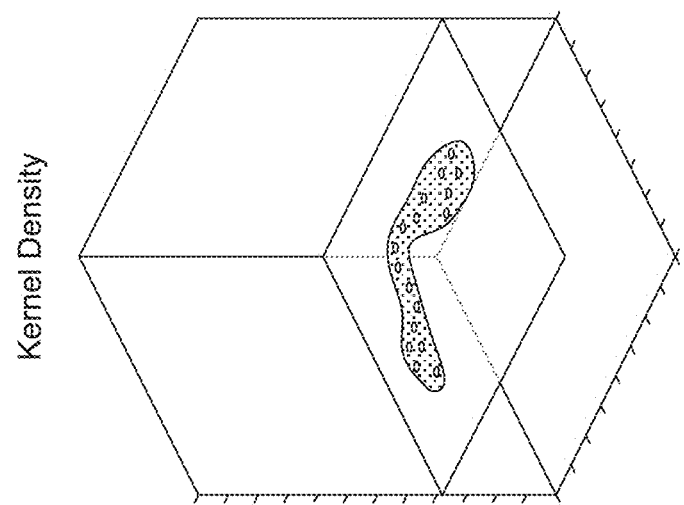
FIGS. 10A-10C are schematics of different statistical distribution types that may be applied for different shapes.
Figure 10B:
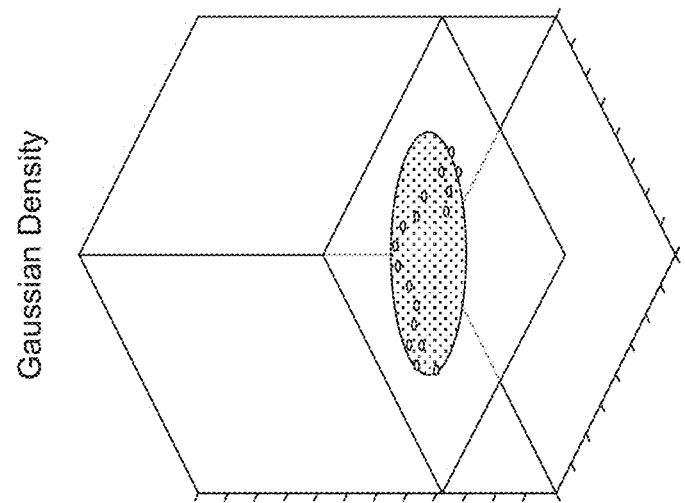
Figure 10A:
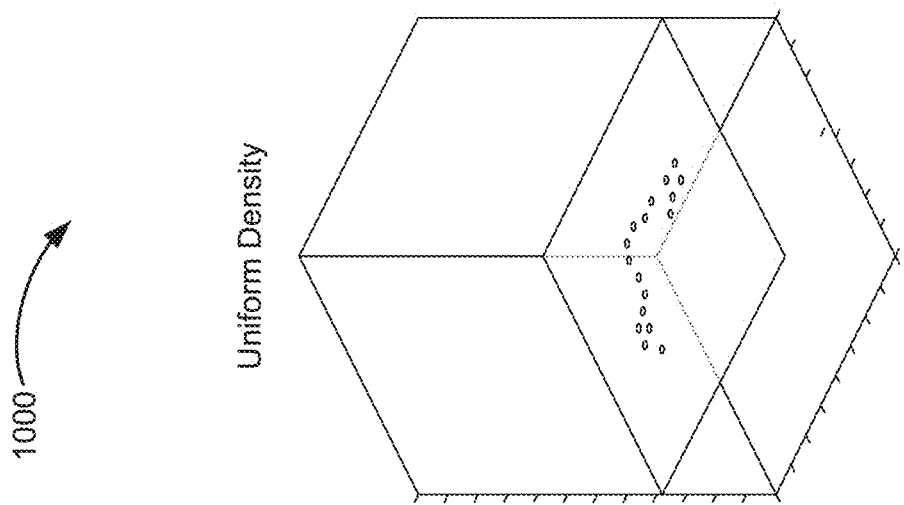

According to implementations used herein, the data-driven statistical shape model may infer a uniform density as shown in the sample of FIG. 10A, a Gaussian distribution as shown in the sample of FIG. 10B, or a kernel density as shown in the sample of FIG. 10C. For uniform distribution, $P(\alpha)$=constant. For Gaussian distribution:

$$\mathcal{P}(\alpha) \propto \exp\left(-\alpha^T \sum\nolimits^{-1} \alpha\right), \text{ where } \sum = \frac{1}{2}\sum_i \alpha_i \alpha_i^T$$

For Kernel distribution:

$$\mathcal{P}(\alpha) = \frac{1}{N\sigma^n}\sum_{i=1}^{N} K\left(\frac{\alpha - \alpha_i}{\sigma}\right),$$

where $$K(u) = \frac{1}{(2\pi)^{n/2}}\exp\left(-\frac{u^2}{2}\right).$$

Figure 11:
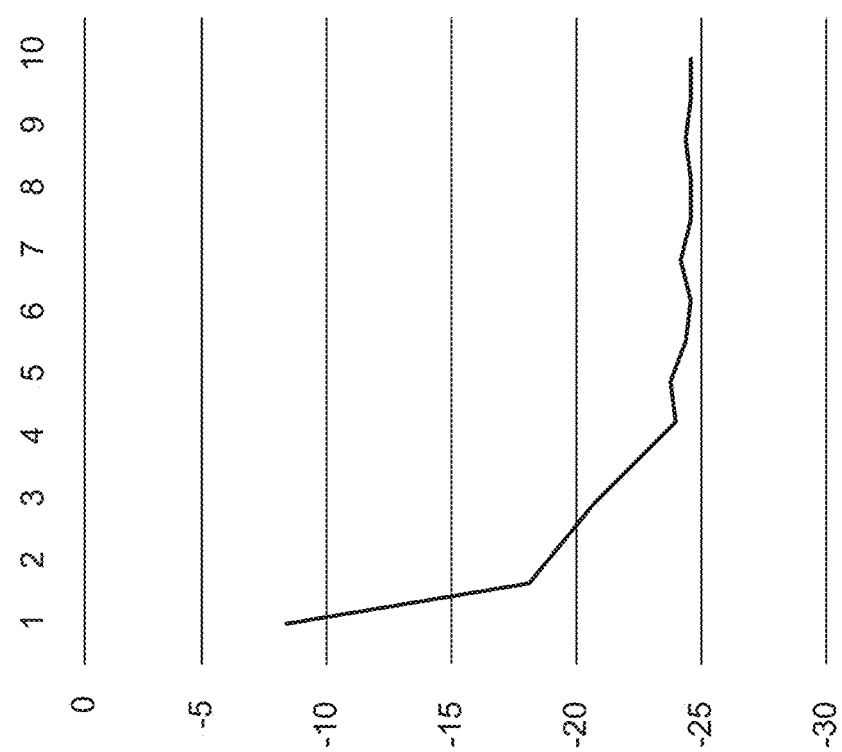
FIG. 11 is simplified energy changing curve that may correspond to minimizing an energy function for a flexible shape model over a target 3D image.

In the example of FIG. 9C, a modified flexible shape model 700-2 is overlaid on target 3D image data set 820. For example, using a data-driven statistical shape model flexible shape model 700-2 may be conformed to the 3D shape of the target image (e.g., phantom 810). FIG. 11 shows an energy changing curve 1100 that may correspond to multiple iterations to minimize the energy function for flexible shape model 700-2 over target 3D image data set 820.

Figure 12:
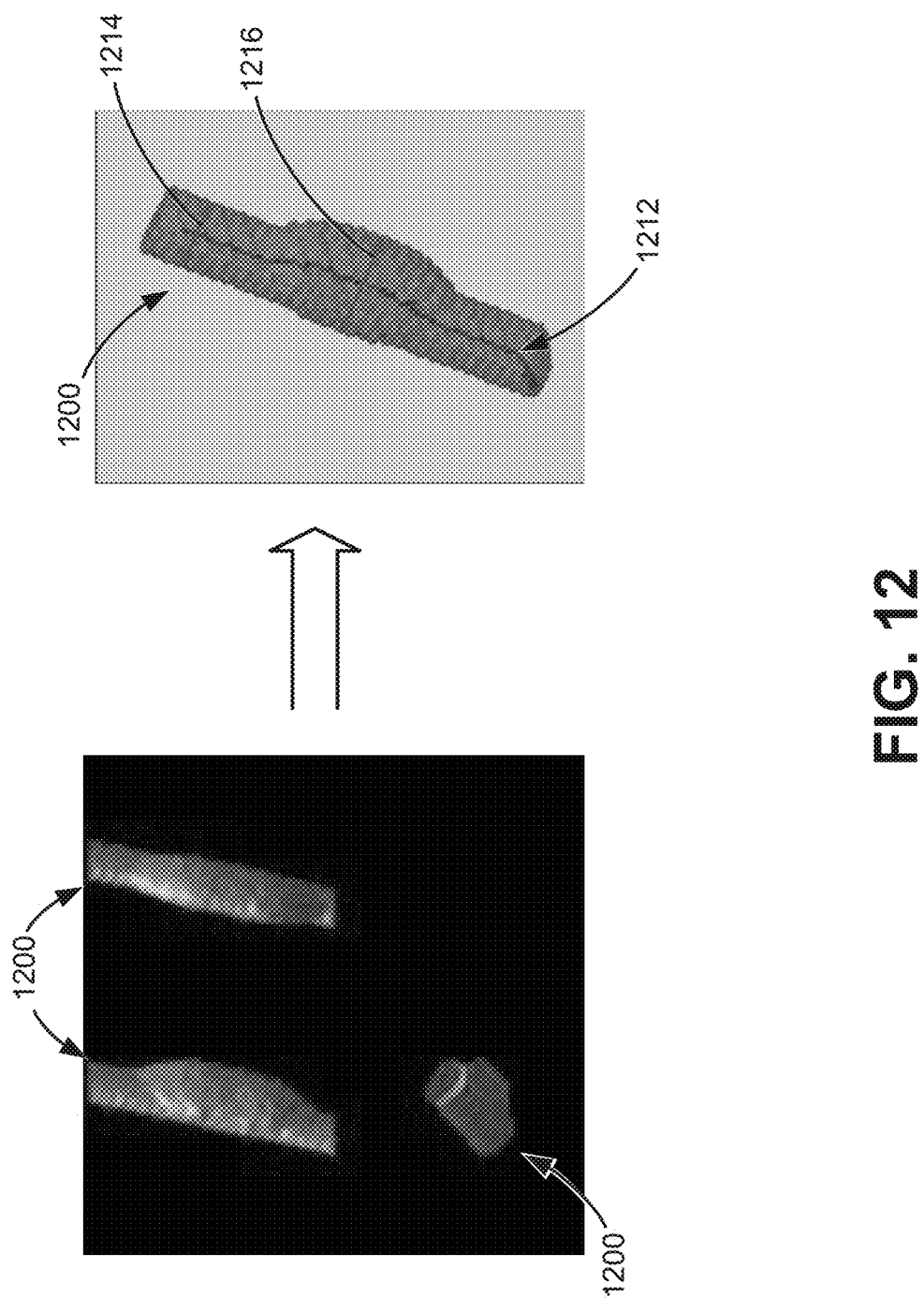
FIG. 12 is a diagram of a model, generated from a best-fit flexible shape model, to measure AAA characteristics.

Returning to FIG. 5, the best fit flexible shape model may be stored as a segmentation result (bock 550) and AAA measurements may be calculated using the stored segmentation result (block 560). For example, the best fit overlay (e.g., flexible shape model 700-2) corresponding to target 3D image data set 820 may be stored for quantitative analysis in an AAA evaluation by post processing unit 240. FIG. 12 illustrates a 3D (e.g., solid) model 1200 that may be generated from a best-fit flexible shape model 700-2. With abdominal aorta segmentation available in the form of 3D model 1200, post processing unit 240 may determine size information for both the aorta and AAA, such as a centerline of the aorta 1212, the diameter of the aorta 1214, the maximum diameter of the aneurysm 1216, and the volume of the aneurysm. Since the AAA is not a tubular structure, the volume of the AAA and/or the ratio of the AAA area to the overall aorta may be a useful quantitative measure. In other implementations, post processing unit 240 may also determine the total area of the aorta and the diameter of the AAA. In each case, post processing unit 240 may output the size and/or area information via, for example, display 122 or via a display 118 on probe 110. Using model 1200 for measurement and analysis enables post processing unit 240 to more easily identify the centerline of the aorta/AAA and determine the correct orientation for measuring the maximum abdominal aorta diameter (e.g., perpendicular to the centerline).

As described above, system 100 may include a probe configured to transmit ultrasound signals directed to a target blood vessel and receive echo information associated with the transmitted ultrasound signals. System 100 may also includes at least one processing device configured to process the received echo information and generating a three-dimensional ultrasound image of the target blood vessel; obtain a flexible three-dimensional vascular model corresponding to the target blood vessel; identify a best-fit of the flexible three-dimensional vascular model onto the three-dimensional target image; store the best fit of the flexible three-dimensional vascular model as a segmentation result; and calculate, based on the segmentation result, measurements for the target blood vessel.

The foregoing description of exemplary implementations provides illustration and description, but is not intended to be exhaustive or to limit the embodiments to the precise form disclosed. Modifications and variations are possible in light of the above teachings or may be acquired from practice of the embodiments.

For example, features have been described above with respect to identifying a target of interest, such as a patient's abdominal aorta and AAA to estimate the size of the target (e.g., the aorta and/or the AAA). In other implementations, other vessels, organs or structures may be identified, and sizes or other parameters associated with the vessels, organs or structures may be estimated. For example, the processing described herein may be used to identify and display a bladder, prostate gland, a kidney, a uterus, ovaries, a heart, etc., as well as particular features associated with these targets, such as area-related measurements.

Further, while series of blocks have been described with respect to FIG. 5, the order of the acts may be different in other implementations. Moreover, non-dependent blocks may be implemented in parallel.

It will be apparent that various features described above may be implemented in many different forms of software, firmware, and hardware in the implementations illustrated in the figures. The actual software code or specialized control hardware used to implement the various features is not limiting. Thus, the operation and behavior of the features were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as one or more processors, microprocessor, application specific integrated circuits, field programmable gate arrays or other processing logic, software, or a combination of hardware and software.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

All structural and functional equivalents to the elements of the various aspects set forth in this disclosure that are known or later come to be known to those of ordinary skill in the art are expressly incorporated herein by reference and are intended to be encompassed by the claims. No claim element of a claim is to be interpreted under 35 U.S.C. § 112(f) unless the claim element expressly includes the phrase "means for" or "step for."

What is claimed is:

1. A system, comprising:
a probe configured to:
transmit ultrasound signals directed to a target blood vessel, and
receive echo information associated with the transmitted ultrasound signals; and
at least one processing device configured to:
process the received echo information and generate a three-dimensional ultrasound image of the target blood vessel,
obtain a flexible three-dimensional vascular model corresponding to the target blood vessel, wherein the flexible three-dimensional vascular model includes a statistical shape model derived from human samples and without using any mesh, and wherein the statistical shape model infers one of a statistical distribution;
perform a shape fitting procedure of the flexible three-dimensional vascular model onto the three-dimensional ultrasound image of the target blood vessel, wherein the shape fitting procedure overlays the flexible three-dimensional vascular model onto the ultrasound image of the target blood vessel and morphs the flexible three-dimensional vascular model to match the ultrasound image of the target blood vessel,
store a segmentation result based on the shape fitting procedure, and
calculate, based on the segmentation result, measurements for the target blood vessel.

2. The system of claim 1, wherein the flexible three-dimensional vascular model corresponds to an abdominal aorta.

3. The system of claim 2, wherein the at least one processing device is further configured to:
determine a longitudinal centerline of the target blood vessel based on the segmentation result.

4. The system of claim 3, wherein, when calculating measurements for the target blood vessel, the at least one processing device is further configured to:
determine a maximum diameter of at least one of the abdominal aorta or an abdominal aortic aneurysm, wherein the maximum diameter is measured perpendicular to the longitudinal centerline.

5. The system of claim 4, further comprising:
a display configured to:
receive the segmentation result,
display an illustration of the segmentation result, and
display the maximum diameter of the abdominal aorta or the maximum diameter of the abdominal aortic aneurysm.

6. The system of claim 1, wherein when performing the shape fitting procedure, the at least one processing device is further configured to:
apply multiple different simulation shapes from the flexible three-dimensional vascular model, wherein each of the multiple simulation shapes includes a simulated aorta data set.

7. The system of claim 6, wherein when performing the shape fitting procedure, the at least one processing device is further configured to:
vary one or more shape model of at least one of the multiple different simulation shapes.

8. The system of claim 1, wherein when performing the shape fitting procedure, the at least one processing device is configured to:
minimize an energy function, which is defined around image data, to fit the flexible three-dimensional vascular model onto the three-dimensional ultrasound image of the target blood vessel.

9. The system of claim 1, wherein when performing the shape fitting procedure, the at least one processing device is further configured to:
vary a tube diameter or a sphere diameter of the flexible three-dimensional vascular model.

10. The system of claim 1, wherein the probe is further configured to:
transmit ultrasound signals directed to the target blood vessel using at least 48 different scan planes from a rotational scan.

11. A method, comprising:
transmitting ultrasound signals directed to a target blood vessel;
receiving echo information associated with the transmitted ultrasound signals;
processing the received echo information and generating a three-dimensional ultrasound image of the target blood vessel;
obtaining a flexible three-dimensional vascular model corresponding to the target blood vessel, wherein the flexible three-dimensional vascular model includes a statistical shape model derived from human samples and without using any mesh, and wherein the statistical shape model infers one of a statistical distribution;
performing a shape fitting procedure of the flexible three-dimensional vascular model onto the three-dimensional ultrasound image of the target blood vessel, wherein the shape fitting procedure overlays the flexible three-dimensional vascular model onto the ultrasound image of the target blood vessel and morphs the flexible three-dimensional vascular model to match the ultrasound image of the target blood vessel;
storing a segmentation result based on the shape fitting procedure; and
calculating, based on the segmentation result, measurements for the target blood vessel.

12. The method of claim 11, wherein the target blood vessel is an abdominal aorta, and wherein calculating the measurements for the target blood vessel comprises:
determining a longitudinal centerline of the target blood vessel based on the three-dimensional vascular model.

13. The method of claim 12, further comprising:
determining a maximum diameter of at least one of the abdominal aorta or an abdominal aortic aneurysm, wherein the maximum diameter is measured perpendicular to the longitudinal centerline.

14. The method of claim 13, further comprising:
outputting image information illustrating one or more of the segmentation result, the maximum diameter of the abdominal aorta, or the maximum diameter of the abdominal aortic aneurysm.

15. The method of claim 11, wherein the target blood vessel is an abdominal aorta, and wherein calculating the measurements for the target blood vessel comprises:
determining a volume of an abdominal aortic aneurysm, on the abdominal aorta, based on the three-dimensional vascular model.

16. The method of claim 11, wherein identifying the best-fit of the flexible three-dimensional vascular model comprises:
applying multiple different simulation shapes from the flexible three-dimensional vascular model, wherein each of the multiple simulation shapes includes a simulated aorta data set.

17. The method of claim 16, wherein identifying the best-fit of the flexible three-dimensional vascular model comprises:
varying one or more of a tube diameter or a sphere diameter of at least one of the multiple different simulation shapes.

18. The method of claim 17, wherein processing the received echo information and generating a three-dimensional ultrasound image comprises:
combining B-mode images from multiple ultrasound cones to obtain the three dimensional ultrasound image.

19. A non-transitory computer-readable medium having stored thereon sequences of instructions which, when executed by at least one processor, cause the at least one processor to:
transmit ultrasound signals directed to a target blood vessel;
receive echo information associated with the transmitted ultrasound signals;
process the received echo information and generating a three-dimensional ultrasound image of the target blood vessel;
obtain a flexible three-dimensional vascular model corresponding to the target blood vessel, wherein the flexible three-dimensional vascular model includes a statistical shape model derived from human samples and without using any mesh, and wherein the statistical shape model infers one of a statistical distribution;
perform a shape fitting procedure of the flexible three-dimensional vascular model onto the three-dimensional ultrasound image of the target blood vessel, wherein the shape fitting procedure overlays the flexible three-dimensional vascular model onto the ultrasound image of the target blood vessel and morphs the flexible three-dimensional vascular model to match the ultrasound image of the target blood vessel;

store a segmentation result based on the shape fitting procedure; and calculate, based on the segmentation result, measurements for the target blood vessel.

20. The non-transitory computer-readable medium of claim 19, wherein the target blood vessel comprises an abdominal aorta, and wherein the instructions further cause the at least one processor to:

determine a longitudinal centerline of the abdominal aorta based on the three-dimensional vascular model.

\* \* \* \* \*